United States Patent
Kim et al.

(10) Patent No.: US 10,542,955 B2
(45) Date of Patent: Jan. 28, 2020

(54) METHOD AND APPARATUS FOR MEDICAL IMAGE REGISTRATION

(71) Applicant: Samsung Electronics Co., Ltd., Suwon-si (KR)

(72) Inventors: Jung-bae Kim, Hwaseong-si (KR); Young-kyoo Hwang, Seoul (KR); Won-chul Bang, Seongnam-si (KR); Young-taek Oh, Seoul (KR); Do-kyoon Kim, Seongnam-si (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 820 days.

(21) Appl. No.: 14/088,787

(22) Filed: Nov. 25, 2013

(65) Prior Publication Data

US 2014/0148690 A1    May 29, 2014

(30) Foreign Application Priority Data

Nov. 26, 2012 (KR) .................. 10-2012-0134868

(51) Int. Cl.
*A61B 6/00* (2006.01)
*A61B 6/12* (2006.01)

(52) U.S. Cl.
CPC .............. *A61B 6/5264* (2013.01); *A61B 6/12* (2013.01)

(58) Field of Classification Search
None
See application file for complete search history.

(56) References Cited

U.S. PATENT DOCUMENTS 6,505,063 B2   1/2003   Van Den Brink et al.
6,650,927 B1   11/2003  Keidar
(Continued)

FOREIGN PATENT DOCUMENTS

EP   1 650 707 A2   4/2006
JP   311834          11/1995
(Continued)

OTHER PUBLICATIONS

Extended European Search Report issued by the European Patent Office dated Apr. 22, 2014 in European Application No. EP 13 19 4482. (7 pages in English).
(Continued)

*Primary Examiner* — Carolyn A Pehlke
*Assistant Examiner* — Marjan Saboktakin
(74) *Attorney, Agent, or Firm* — Cha & Reiter, LLC

(57) ABSTRACT

A method of medical image registration with respect to a volume of interest (VOI) and an apparatus for performing the method are provided. In one embodiment, the method includes obtaining a first medical image of a selected section of the VOI, from a first medical apparatus, detecting a sectional image corresponding to the selected section from second medical images previously captured of the VOI, based on an anatomical feature appearing in the first medical image, mapping virtual coordinate schemes of the first and second medical images to produce a mapped virtual coordinate scheme, based on the detected sectional image and the first medical image, and tracking a movement of a section of the VOI captured by the first medical apparatus in the second medical images by using a mapped virtual coordinate scheme.

22 Claims, 12 Drawing Sheets

(56) References Cited

U.S. PATENT DOCUMENTS

| | | | |
|---|---|---|---|
| 8,165,372 B2 | 4/2012 | Ishikawa et al. | |
| 8,606,045 B2 | 12/2013 | Lee | |
| 2008/0085042 A1* | 4/2008 | Trofimov | A61B 5/042 382/128 |
| 2009/0097778 A1* | 4/2009 | Washburn | G06T 7/0028 382/294 |
| 2010/0239150 A1 | 9/2010 | Ishikawa et al. | |
| 2011/0028843 A1* | 2/2011 | Hyun | G06T 7/0038 600/443 |
| 2011/0028844 A1 | 2/2011 | Hyun et al. | |
| 2012/0253170 A1 | 10/2012 | Kim et al. | |

FOREIGN PATENT DOCUMENTS

| | | |
|---|---|---|
| JP | 131403 | 5/1996 |
| JP | 9-24034 | 1/1997 |
| JP | 9-84746 | 3/1997 |
| JP | 3871747 | 10/2006 |
| JP | 3878456 | 11/2006 |
| KR | 10-2002-0014751 A | 2/2002 |
| KR | 10-2009-0127091 A | 12/2009 |
| KR | 10-2010-0062889 A | 6/2010 |
| KR | 10-2011-0013026 A | 2/2011 |
| KR | 10-2011-0013738 A | 2/2011 |
| KR | 10-1017610 | 2/2011 |
| KR | 10-1017611 | 2/2011 |
| KR | 10-2011-0078274 | 7/2011 |
| KR | 10-1118549 | 2/2012 |
| KR | 10-1117026 | 3/2012 |
| KR | 10-1121286 | 3/2012 |
| KR | 10-1121353 | 3/2012 |
| KR | 10-1121396 | 3/2012 |
| KR | 10-11325536 | 3/2012 |
| KR | 10-2012-0111871 A | 10/2012 |
| WO | 2010/064348 A1 | 6/2010 |

OTHER PUBLICATIONS

Brown, Lisa Gottesfeld. "A survey of image registration techniques." ACM computing surveys (CSUR) 24.4 (Dec. 1992): 325-376.

Maintz, J. B., and Max A. Viergever. "A survey of medical image registration." Medical image analysis 2.1 (Mar. 1998): 1-36.

Pham, Dzung L., Chenyang Xu, and Jerry L. Prince. "Current methods in medical image segmentation 1." Annual review of biomedical engineering 2.1 (Aug. 2000): 315-337.

Zitova, Barbara, and Jan Flusser. "Image registration methods: a survey." *Image and vision computing* 21.11 (Oct. 2003): 977-1000.

Zhang, Qi, Roy Eagleson, and Terry M. Peters. "GPU-based visualization and synchronization of 4-D cardiac MR and ultrasound images." Information Technology in Biomedicine, IEEE Transactions on 16.5 (Jun. 2012): 878-890.

Korean Notice of Allowance dated May 10, 2019.

\* cited by examiner

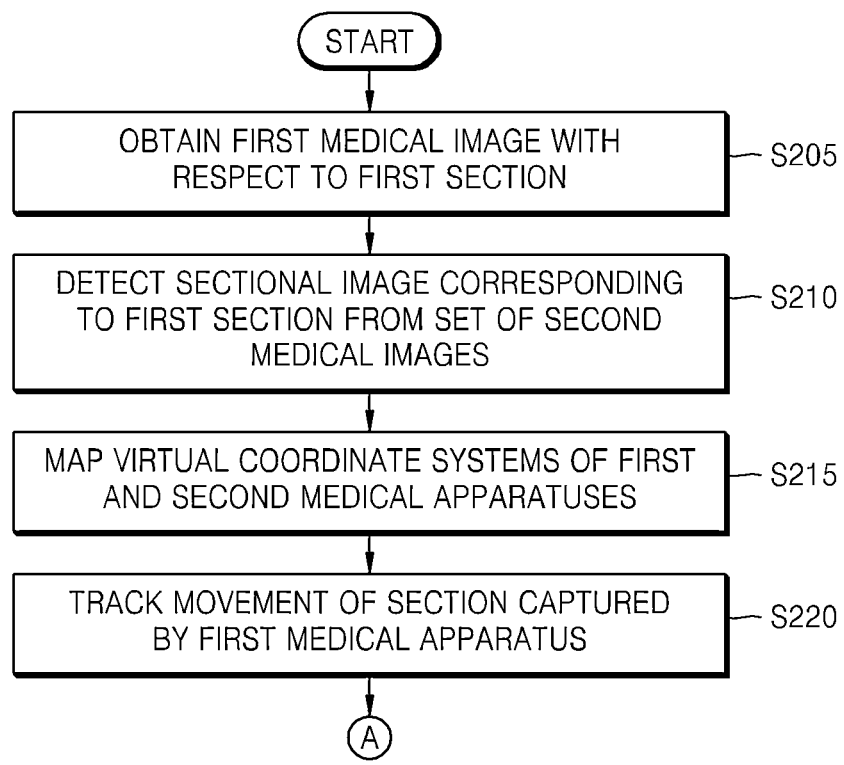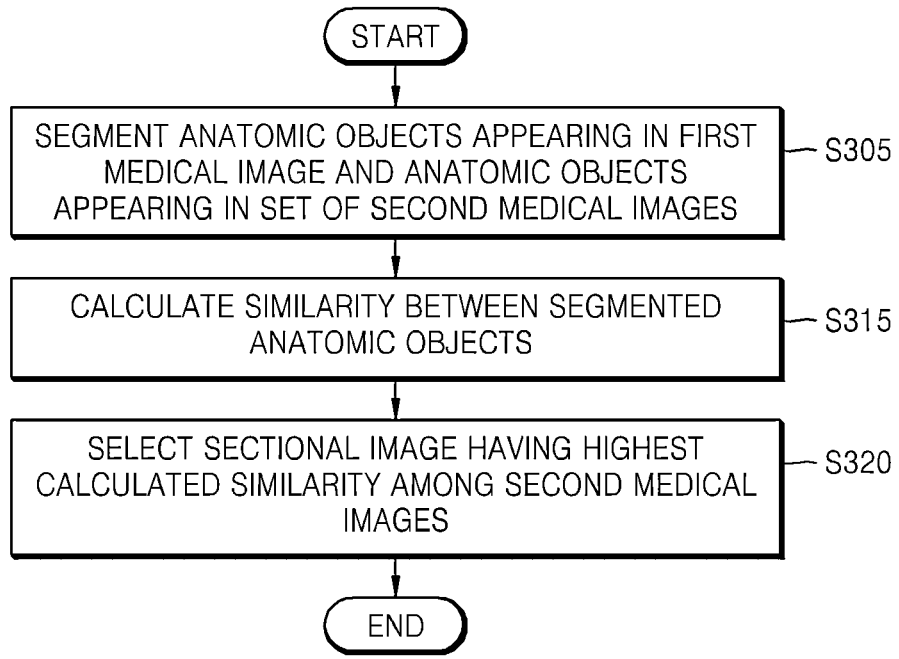

METHOD AND APPARATUS FOR MEDICAL IMAGE REGISTRATION

CROSS-REFERENCE TO RELATED APPLICATIONS

This application claims the benefit of Korean Patent Application No. 10-2012-0134868 filed on Nov. 26, 2012, in the Korean Intellectual Property Office, the entire disclosure of which is incorporated herein by reference for all purposes.

BACKGROUND

1. Field

The following description relates to a method and apparatus to register a plurality of medical images. Specifically, the method and apparatus map sections from corresponding medical images from different sources to one another.

2. Description of the Related Art

With recent developments in medical technologies, high definition medical images of patients are available. Also fine manipulation of medical equipment and devices has become possible. Accordingly, a method of treating a patient by directly forming a small hole in his or her skin without making a direct incision into a human body, such as by inserting a catheter or a medical needle into the human body, and observing the inside of the human body by using medical imaging equipment is being actively developed. The method is referred to as a medical treatment method using an image or an interventional image medical treatment method. In this approach, a medical practitioner recognizes the position of an organ or a lesion through an image provided by the medical imaging equipment.

In addition, the medical practitioner recognizes a change in the patient according to patient's breathing patterns or movement during a medical treatment. Thus, the medical practitioner needs to accurately and quickly recognize that breathing or movement occurs, based on a real-time image of the patient. However, it is difficult to clearly identify the shapes of an organ or a lesion from a real-time image with the naked eye because real-time images may be limited to images such as ultrasonic wave images that lack sharpness and/or clarity.

In contrast to an ultrasonic wave image, a magnetic resonance (MR) image or a computed tomography (CT) image may be sharper to clearly distinguish the shape of an organ or a lesion in the image. However, since an MR or CT image may not be obtained in real time during a medical treatment, effects on the shapes and positions on organs or lesions resulting from the breathing and moving of a patient during the medical treatment may not be reflected.

SUMMARY

Provided is a method and apparatus for accurately and quickly registering medical images captured by a first medical apparatus and a second medical apparatus by mapping virtual coordinate systems used by the first medical apparatus for capturing a medical image during a medical treatment and by the second medical apparatus for capturing a medical image before the medical treatment.

Provided is a computer readable recording medium having recorded thereon a program for executing the above method.

Additional aspects will be set forth in part in the description which follows and, in part, will be apparent from the description, or may be learned by practice of the presented embodiments.

According to an aspect of the present invention, there is provided a method of medical image registration with respect to a volume of interest (VOI), including obtaining a first medical image of a selected section of the VOI, from a first medical apparatus, detecting a sectional image corresponding to the selected section from second medical images previously captured of the VOI, based on an anatomical feature appearing in the first medical image, mapping virtual coordinate schemes of the first and second medical images to produce a mapped virtual coordinate scheme, based on the detected sectional image and the first medical image, and tracking a movement of a section of the VOI captured by the first medical apparatus in the second medical images by using a mapped virtual coordinate scheme.

In an embodiment, the first medical image is associated with a first virtual coordinate scheme, the second medical images are captured by a second medical apparatus, the second medical apparatus being associated with a second virtual coordinate scheme, and the mapping of the virtual coordinate scheme comprises mapping the first and the second virtual coordinate schemes.

In an embodiment, the detecting of the sectional image includes detecting the sectional image based on a similarity between the anatomical features appearing in the first medical image and the second medical images.

In an embodiment, the detecting of the sectional image includes segmenting anatomic objects appearing in the first medical image and anatomic objects appearing in the second medical images, calculating a similarity between the segmented anatomic objects in the first medical image and the segmented anatomic objects in the second medical images, and selecting a sectional image having the highest calculated similarity among the second medical images.

In an embodiment, the segmenting of the anatomic objects includes segmenting at least one of organs, blood vessels, and lesions appearing in the first medical image and the second medical images based on at least one of a graph cut technique and a Gaussian mixture model (GMM) technique, and the calculating of the similarity includes calculating the similarity between the segmented anatomic objects based on at least one of a Gabor wavelet technique and a local binary pattern matching technique.

In an embodiment, the mapping of the virtual coordinates systems includes detecting a second position in the virtual coordinate system of the second medical apparatus corresponding to a first position in the virtual coordinate system of the first medical apparatus, wherein the first position indicates a location of a probe included in the first medical apparatus, and generating a coordinate conversion function to convert the virtual coordinate system of the first medical apparatus to the virtual coordinate system of the second medical apparatus by using a coordinate value of the second position, and the tracking of the movement of a section includes tracking the movement of the section by using the generated coordinate conversion function.

In an embodiment, the method further includes obtaining a third medical image captured by the first medical apparatus with respect to a second section selected in the VOI, extracting a first landmark point from the third medical image, detecting a second landmark point corresponding to the extracted first landmark point from the second medical images, and correcting the mapped virtual coordinate system based on the extracted first landmark point and the detected second landmark point.

In an embodiment, the detecting of the second landmark point includes reconstructing a three-dimensional (3D) model with respect to the VOI by using the second medical images, segmenting each of anatomic objects appearing in a reconstructed 3D model and the third medical image, and detecting the second landmark point corresponding to the first landmark point from the reconstructed 3D model by comparing the segmented anatomic objects in the reconstructed 3D model and the third medical image.

In an embodiment, in the correcting of the mapped virtual coordinate system, a coordinate conversion function is corrected such that the first landmark point and the second landmark point are matched with each other, and in the tracking of the movement of the section, the movement of the section is tracked by using a corrected coordinate conversion function.

In an embodiment, the tracking of the movement of the section includes obtaining a fourth medical image captured by the first medical apparatus with respect to a third section as a probe of the first medical apparatus moves, converting a coordinate value of a position of the probe of the first medical apparatus during capturing of the fourth medical image to a coordinate value of the virtual coordinate system of the second medical apparatus based on the mapped virtual coordinate system, and reconstructing a sectional image with respect to the third section from the second medical images based on a converted coordinate value.

In an embodiment, the method further includes outputting the fourth medical image and a reconstructed sectional image with respect to the third section.

In another aspect, there is provided an apparatus for medical image registration, including a first medical apparatus configured to obtain a first medical image of a selected section of a volume of interest (VOI), a detector configured to detect a sectional image corresponding to the selected section from second medical images previously captured of the VOI, based on an anatomical feature appearing in the first medical image, a coordinate converter configured to map virtual coordinate systems of the first and second medical images to produce a mapped virtual coordinate scheme, based on the detected sectional image and the first medical image, and an image outputter configured to track a movement of a section of the VOI captured by the first medical apparatus in the second medical images by using a mapped virtual coordinate scheme.

In an embodiment, the first medical image is associated with a first virtual coordinate scheme, the second medical images are captured by a second medical apparatus, the second medical apparatus being associated with a second virtual coordinate scheme, and the coordinate converter is configured to map the first and the second virtual coordinate schemes.

In an embodiment, the detector is configured to detect the sectional image based on a similarity between the anatomical features appearing in the first medical image and the second medical images.

In an embodiment, the detector includes an image segmenter configured to segment anatomic objects appearing in the first medical image and anatomic objects appearing in the second medical images, and a sectional image detector configured to calculate a similarity between the segmented anatomic objects in the first medical image and the segmented anatomic objects in the set of second medical images, and select a sectional image having the highest calculated similarity among the set of second medical images.

In an embodiment, the image segmenter is configured to segment at least one of organs, blood vessels, and lesions appearing in the first medical image and the second medical images based on at least one of a graph cut technique and a Gaussian mixture model (GMM) technique, and the sectional image detector is configured to calculate the similarity between the segmented anatomic objects based on at least one of a Gabor wavelet technique and a local binary pattern matching technique.

In an embodiment, the coordinate converter includes a reference point detector configured to detect a second position in the virtual coordinate system of the second medical apparatus corresponding to a first position in the virtual coordinate system of the first medical apparatus, wherein the first position indicates a location of a probe included in the first medical apparatus, and a conversion function generator configured to generate a coordinate conversion function to convert the virtual coordinate system of the first medical apparatus to the virtual coordinate system of the second medical apparatus by using a coordinate value of the second position, and the image outputter is configured to track the movement of the section by using the generated coordinate conversion function.

In an embodiment, the first medical image obtainer is configured to obtain a third medical image captured by the first medical apparatus with respect to a second section selected in the VOI, the detector is configured to extract a first landmark point from the third medical image and configured to detect a second landmark point corresponding to the extracted first landmark point from the set of second medical images, and the coordinate converter is configured to correct the mapped virtual coordinate system based on the extracted first landmark point and the detected second landmark point.

In an embodiment, the image outputter is configured to reconstruct a three-dimensional (3D) model with respect to the VOI by using the set of second medical images, and the detector includes an image segmenter configured to segment each of anatomic objects appearing in a reconstructed 3D model and the third medical image, and a landmark point detector configured to detect the second landmark point corresponding to the first landmark point from the reconstructed 3D model by comparing the segmented anatomic objects in the reconstructed 3D model and the third medical image.

In an embodiment, the coordinate converter is configured to correct a coordinate conversion function such that the first landmark point and the second landmark point are matched with each other, and the image outputter is configured to track the movement of the section by using a corrected coordinate conversion function.

In an embodiment, the first medical image obtainer is configured to obtain a fourth medical image captured by the first medical apparatus with respect to a third section as a probe of the first medical apparatus moves, the coordinate converter is configured to convert a coordinate value of a position of the probe of the first medical apparatus during capturing of the fourth medical image to a coordinate value of the virtual coordinate system of the second medical apparatus based on the mapped virtual coordinate system, and the image outputter is configured to reconstruct a sectional image with respect to the third section from the set of second medical images based on a converted coordinate value.

In an embodiment, the image outputter is configured to output the fourth medical image and a reconstructed sectional image with respect to the third section.

In yet another aspect, there is provided an apparatus for medical image registration, including a detector configured to identify a second sectional image corresponding to a first sectional image of a volume of interest (VOI) produced by a first medical apparatus, chosen from previous medical images of the VOI, and a coordinate converter configured to receive an additional sectional image from the first medical apparatus, and map the additional sectional image to another previous medical image of the VOI, based on motion data from the first medical apparatus and a mapping between virtual coordinate schemes of the first sectional image and the second sectional image.

In an embodiment, the second sectional image is chosen based on a feature of the VOI.

In an embodiment, the second sectional image is chosen based on a similarity between the anatomical features appearing the first sectional image and the previous medical images.

In an embodiment, the previous medical images are obtained by a second medical apparatus and the previous medical images are associated with a second virtual coordinate scheme.

BRIEF DESCRIPTION OF THE DRAWINGS

FIG. 2 is a flowchart illustrating a medical image registration method according to an embodiment of the present invention.

FIG. 3 is a flowchart illustrating a plane matching method in the medical image registration method of FIG. 2.

DETAILED DESCRIPTION

Figure 1:
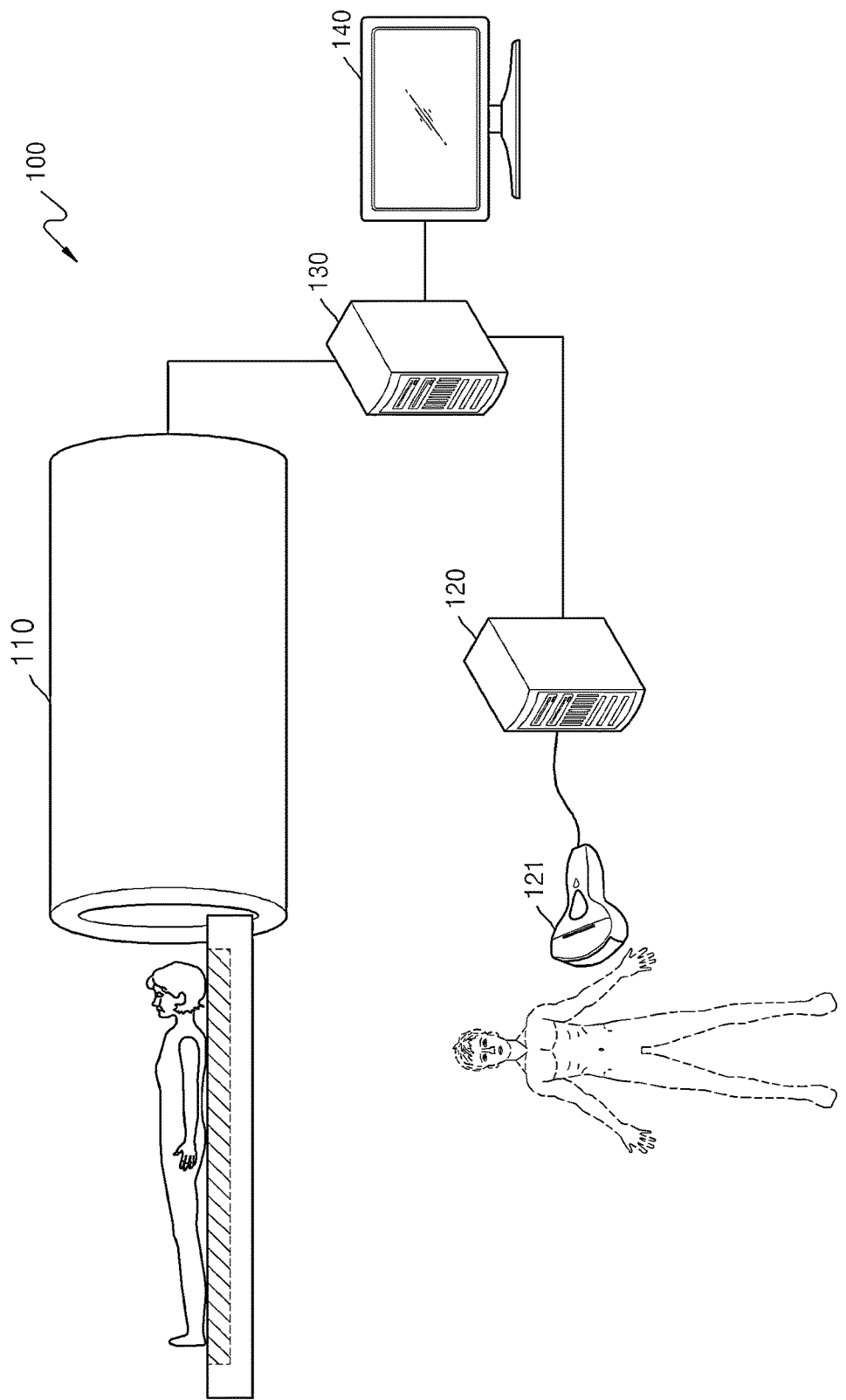
FIG. 1 illustrates a structure of a medical image registration system according to an embodiment of the present invention.

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

As used herein, the term "and/or" includes any and all combinations of one or more of the associated listed items. Expressions such as "at least one of," when preceding a list of elements, modify the entire list of elements and do not modify the individual elements of the list.

Virtual coordinate systems, as discussed in the specification, have been referred to as "systems." Such coordinate systems include two or three perpendicular axes with a certain origin and orientation that allow the location of points on a plane or in space to be identified. However, such coordinate systems have also been referred to as coordinate "schemes" in order to clarify that these "coordinate schemes" are geometrical constructions for specifying locations rather than apparatuses or machines.

FIG. 1 illustrates a structure of a medical image registration system 100 according to an embodiment of the present invention. Referring to FIG. 1, the medical image registration system 100 according to the present embodiment includes a first medical apparatus 120, a second medical apparatus 110, a medical image registration apparatus 130, and an image display apparatus 140.

The second medical apparatus 110 generates a set of second medical images with respect to a volume of interest (VOI) of an object before a medical treatment. A VOI refers to a three-dimensional region, such as the interior of a patient, the distribution of whose contents is desired to be known. In an example, the second medical apparatus 110 is a medical scanning device that generates a set of second medical images that depict the interior of the body of a patient. In embodiments, the second medical apparatus 110 is a computed tomography (CT) imaging apparatus or a magnetic resonance (MR) imaging apparatus, but other appropriate second medical apparatus 110 scanners may be used to generate the set of second medical images of the VOI. Such a scanner obtains data from an X-ray imaging apparatus, a positron emission tomography (PET) imaging apparatus, or another apparatus that uses radiation of some type to generate scans of the patient.

In the following description, for convenience of explanation, it is assumed that second medical images are MR images or CT images as discussed above. However, other embodiments use other image types that provide similar image quality. A CT image or a MR image generated by the second medical apparatus 110 characteristically clearly distinguishes a position of an organ and a position of a lesion, due to having good image clarity and definition.

However, the CT or MR image may not incorporate real-time changes into the images that occur as a patient breathes or moves during a medical treatment which may deform or change organs. Each of these types of images present separate issues that make it difficult to use these imaging techniques in real-time.

The reason for not being able to output an image in real time is that, in the case of a CT image, the image capturing technique uses a radioactive ray. If multiple CT images were obtained over an extended period of time, such a use of CT technology would lead to the risk that a patient and a medical practitioner would be exposed to a radioactive ray for a long time. Hence, such an extended use of CT imagery is not a safe approach. In the case of an MR image, the reason why the technology is inappropriate for real-time imaging is simply that the nature of this technology dictates that obtaining each image takes an extended period of time, so MR imagery cannot accumulate enough images in a given period of time to be able to serve as a real-time image source.

The first medical apparatus 120 provides a medical image in real time with respect to a VOI of an object. In an embodiment, the first medical apparatus 120 is formed of an ultrasonography machine for generating a real-time image during an ongoing interventional medical treatment process with respect to a patient. The first medical apparatus 120 emits an ultrasonic wave signal to an area of interest by using a probe 121 connected to the first medical apparatus 120 and detects and processes a reflected ultrasonic wave signal to generate an ultrasonic wave image. In an embodiment, the probe 121 is formed of a piezoelectric transducer.

When an ultrasonic wave of a magnitude of hundreds of mega hertz is transmitted to a particular portion inside the body of a patient the probe 121, the ultrasonic wave is partially reflected from boundaries between various different tissues. In particular, the ultrasonic wave is reflected from regions where there is a change in density in the inside of a human body, for example, blood cells in blood plasma or small structures in organs. The reflected ultrasonic wave vibrates the piezoelectric transducer of the probe 121 and the piezoelectric transducer outputs electrical pulses according to the vibrations. The electric pulses are transformed into a digital bitstream that represents the signal received by the probe 121. The digital bitstream can be processed and organized so that the first medical apparatus 120 can merge the data from the probe 121 into information associating areas of the patient's body with densities. The densities may be processed into a representation of what was scanned. As such, the electrical pulses are converted into image data.

As described above, a real-time image such as an ultrasonic image may include much noise due to attributes of the scanning technology being used and thus the noise makes it difficult to identify an outline, an internal structure, or a lesion of an organ. Since a lesion and a peripheral tissue have a similar response to ultrasonic waves, a contrast at a boundary between a lesion and a peripheral tissue in an ultrasonic wave image, that is, an edge contrast of an object, is relatively low. Also, noise and artifacts in the original image exist due to interference and diffusion of ultrasonic waves, making it even more difficult to derive useful information from an ultrasound image.

In other words, although the ultrasonic wave medical image may be obtained more quickly than an MR or CT image, sometimes an organ and a lesion that are distinguishable in the MR or CT image are not clearly distinguished from the peripheral tissue in a corresponding ultrasonic wave medical image because a signal to noise ratio (SNR) and the edge contrast of an object are low in the corresponding ultrasonic wave medical image.

In some embodiments, the medical images captured by the first and second medical apparatuses 120 and 110 are two-dimensional (2D) sectional images of the interior of the patient's body. However, in another embodiment, a three-dimensional (3D) medical image is generated by accumulating the 2D sectional images and processing them to generate a 3D image. For example, the second medical apparatus 110 captures a plurality of sectional images by changing the position and orientation of each sectional image. Each of these sectional images portrays a slightly different perspective of the interior of the patient's body.

When the sectional images are accumulated, image data representing a 3D volume corresponding to a particular portion of a patient's body in 3D is generated. The above method of generating image data of a 3D volume by accumulating sectional images is referred to as a multiplanar reconstruction (MPR) method. In particular, although each of the original second medical images is a 2D image, each of pixels of a 2D image is associated with a depth value. In other words, the second medical images are formed of voxels, because the depth values characterize the 3D aspects of the medical images. Thus, a 3D model of a VOI may be generated by accumulating the second medical images by using the image data and its associated depth information.

The medical image registration apparatus 130 matches a set of the second medical images obtained from the second medical apparatus 110 and a first medical image obtained from the first medical apparatus 120 to one another based on which of the sets of medical images correspond to the same subjects. In the present invention, registration of the first and second medical images includes a process of matching virtual coordinate systems respectively used by the first and second medical apparatuses 120 and 110. The virtual coordinate systems establish which portions of the various images correspond to one another.

Each of the virtual coordinate systems identifies a 3D position in a real space with respect to where the first and second medical apparatuses 120 and 110 are located. More specifically, each of the virtual coordinate systems establishes a correspondence between features of the images produced by the first and second medical apparatuses 120 and 110 and to locations of those features in the volume of interest in the interior of the patient. Since the first and second medical apparatuses 120 and 110 are located at different places and are not used at the same time, the first and second medical apparatuses 120 and 110 each use different virtual coordinate systems.

In an embodiment, a registered medical image is a medical image in which the first and second medical images are overlaid or an image in which the first and second medical images having the same view are arranged parallel to each other. In general, the goal of producing a registered medical image is to match individual images from the first and second medical images to one another to establish correspondence between their features. The medical image matched by the medical image registration apparatus 130 is displayed by the image display apparatus 140.

In an embodiment, the medical image registration apparatus 130 matches and aligns the medical images captured by the first and second medical apparatuses 120 and 110 by mapping corresponding portions of the different virtual coordinate systems of the first and second medical apparatuses 120 and 110 to each other. 3-axis position information (x, y, z) and 3-axis rotation information (roll, pitch, yaw) are used to determine a section from which a medical image is captured in the virtual coordinate systems used by the first and second medical apparatuses 120 and 110. By aligning the position and rotation of the axes in the sets of medical information, embodiments are able to determine which portions of images from one set correspond to portions of images from the other set.

A position in a 3D space where a medical image is captured may be specified by the virtual coordinate systems used by the first and second medical apparatuses 120 and 110, as discussed above. For an MR or CT image, coordinate values of a virtual coordinate system are used in a process of selecting a particular section to be captured by the second medical apparatus 110, in that an image to be captured is produced with its relationship to the virtual coordinate system being predetermined. Thus, the coordinate values of the medical image captured by the second medical apparatus 110 may be identified with no additional sensing.

By contrast, in the first medical apparatus 120, the position of a section to be captured varies in real-time according to a movement of the probe 121. The probe 121 is moved not by the control of the first medical apparatus 120, but by the control of a medical operator. For example, the probe 121 may be held in the hand of a medical operator and moved into various positions in proximity to the user's body to provide various scans of the user's body as the probe 121 is repositioned. Accordingly, in order to identify where a medical image captured by the first medical apparatus 120 is located in a virtual coordinate system, the movement of the probe 121 is sensed. Information about the movement of the probe 121 can allow the first medical apparatus 120 to infer how to align information produced by the probe 121 appropriately with the virtual coordinate system.

Various ways are used in various embodiments to sense the movement of the probe 121. In various embodiments, a method of sensing a change in a magnetic field by using a magnetic tracker in the probe 121 or a method of sensing an optical change with an infrared or color camera by attaching an optical marker to the probe 121 are used. However, other embodiments use other relevant approaches to sense the movement of the probe 121.

The first and second medical apparatuses 120 and 110 generally use different 3D coordinate systems because they usually portray slightly different sections of the user's body. Thus, a section 1011, in FIG. 10, in a coordinate system used by the first medical apparatus 120 is specified by using the 3-axis position information (x, y, z) of a position B1 and the 3-axis rotation information (roll, pitch, yaw) of the probe 121.

FIG. 2 is a flowchart illustrating a medical image registration method according to an embodiment of the present invention. Before describing the method of FIG. 2, it is assumed that a set of the second medical images captured by the second medical apparatus 110 with respect to a VOI is already stored in the medical image registration apparatus 130.

Figure 10:
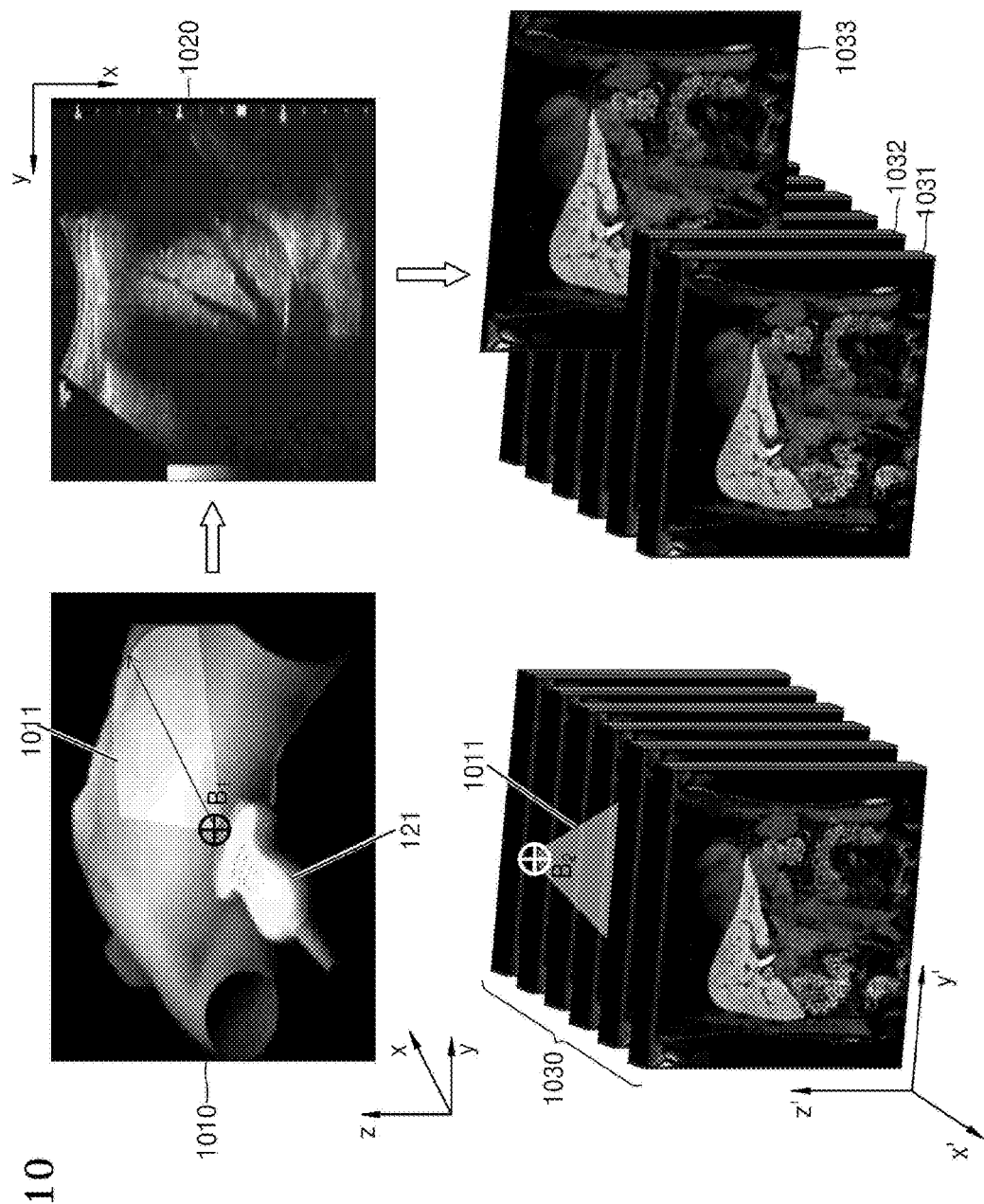
FIG. 10 is an example set of medical images in a plane matching process in the medical image registration method of FIG. 2.

First, the medical image registration apparatus 130 obtains a first medical image captured by the first medical apparatus 120 with respect to a first section selected in the VOI (S205). The first section is a section selected during the capturing by the first medical apparatus 120. For example, a user selects a section in a direction parallel to a section along which the second medical images are captured. Obtaining sectional images that are parallel to one another improves accuracy when a sectional image corresponding to the first section is detected from the set of second medical images, as will be described later, because it requires less processing and manipulation to align the images. The first section is selected based on a user input. For example, the user inputs a selection of the first section through the first medical apparatus 120 or the medical image registration apparatus 130. In FIG. 10, the section 1011 of the image 1010 is a first section selected by a user and a medical image 1020 is a first medical image captured by the first medical apparatus 120.

The medical image registration apparatus 130 detects a sectional image corresponding to the first section from the set of second medical images previously captured with respect to the VOI based on an anatomical feature of the first medical image (S210). In other words, the medical image registration apparatus 130 compares anatomical features contained within the first medical image and anatomical features contained within the set of second medical images and detects a sectional image having the largest similarity to the first medical image from within the set of second medical images. Referring to FIG. 10, medical images 1030 correspond to the set of second medical images, which are candidates for the detection process. The medical image registration apparatus 130 detects a medical image 1033 having the largest similarity to the medical image 1020, of the medical images 1030, as a sectional image corresponding to the section 1011.

FIG. 3 is a flowchart illustrating a plane matching method in the medical image registration method of FIG. 2. Referring to FIG. 3, operation S210 is described in detail.

The medical image registration apparatus 130 segments the anatomic objects in the first medical image and anatomic objects in the set of second medical images (S305). In an embodiment, the anatomic objects are parts of a human body such as organs, blood vessels, lesions, and bones, or boundaries between organs, which are distinguishable in the first medical image. The segmentation refers to separation of each anatomic object from a background image. Information about the anatomic object to be segmented is input to the medical image registration apparatus 130 in advance, and such information is used to facilitate the segmenting. For example, for an ultrasonic wave medical image, information indicating that a blood vessel has a darker brightness value than a background is previously input and is used to distinguish blood vessels. Also, information about anatomical features, for example, a diaphragm, which is a plane having a curvature of a predetermined value or lower, and an inferior vena cava, which is a blood vessel having a diameter of 10 mm or higher, is input in advance, and used when processing the first medical image to perform the segmenting.

For example, the medical image registration apparatus 130 performs segmentation by a graph cut technique or a Gaussian mixture model (GMM) technique. According to the graph cut technique, the medical image registration apparatus 130 gradually extends areas of a seed point of a background and a seed point of an anatomic object by using a seed value of a background and a seed value of an anatomic object. In doing so, the medical image registration apparatus 130 determines a boundary where a background area and the area of an anatomic object meet and the medical image registration apparatus 130 segments the anatomic object appropriately. According to the GMM technique, the medical image registration apparatus 130 uses a color histogram of a medical image. In the GMM technique, the color histogram is expressed by a plurality of Gaussian distribution models. Then, the medical image registration apparatus 130 segments anatomic objects by selecting a Gaussian distribution model in a particular band in the histogram. In other embodiments, other appropriate segmentation techniques differing from the above-described techniques are used.

The medical image registration apparatus 130 calculates the similarity between the anatomic object segmented in the set of second medical images and the anatomic object segmented in the set of first medical images (S310). In an embodiment, the similarity is determined to be a numerical value, though other embodiments use other indicators to express similarity. For example, the medical image registration apparatus 130 calculates the similarity numerically.

Certain embodiments use various techniques for calculating a numerical value for similarity. In embodiments, the medical image registration apparatus 130 calculates the similarity by using a Gabor wavelet technique or a local binary pattern matching technique. According to the Gabor wavelet technique, the medical image registration apparatus 130 filters anatomic objects using Gabor filters having various different filtering characteristics and the medical image registration apparatus 130 compares the results of the filtering to each other. According to the local binary pattern matching technique, the medical image registration apparatus 130 defines a relationship between peripheral pixels around one center pixel. The medical image registration apparatus 130 binarizes values of the peripheral pixels with respect to a value of a center pixel. The medical image registration apparatus 130 then arranges the results in a preset direction. As such, by comparing the binary results, the similarity between the anatomic objects is quantitatively evaluated.

The medical image registration apparatus 130 selects a sectional image having the highest calculated similarity among the set of second medical images (S320). In other words, the medical image registration apparatus 130 selects a sectional image having the most similar anatomical feature to the first medical image, in the set of second medical images. As discussed above, various measures will indicate which image from the set of second medical images is the image with the highest calculated similarity, and that image will be the most useful image because it is most likely to portray the same subject matter as the first medical image.

Figure 12:
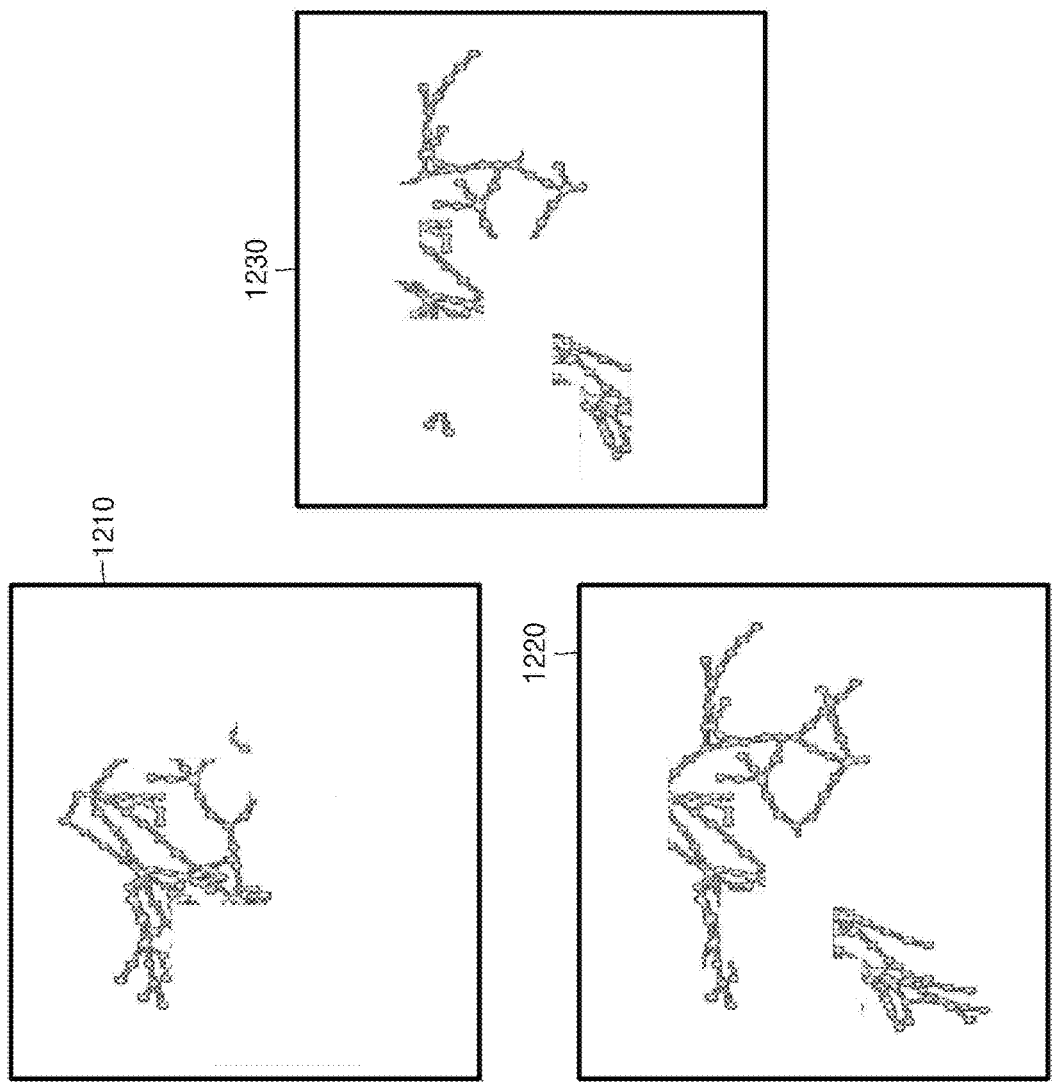
FIG. 12 is an example set of medical images of anatomical objects segmented in the medical image registration method of FIG. 2.

Referring to FIG. 12, images 1210 and 1220 illustrate blood vessels segmented in the set of second medical images and an image 1230 illustrates blood vessels segmented in the first medical image. The images 1210 and 1220 are segmented from different sectional images in the set of second medical images. The medical image registration apparatus 130 calculates a similarity between the images 1230 and 1210 and calculates a similarity between the images 1230 and 1220. As a result, since the image 1220 is more similar to the image 1230 than the image 1210, the similarity between the images 1230 and 1220 results in selection of the sectional image including the image 1220 as the image with the highest calculated similarity.

Referring back to FIG. 2, the medical image registration apparatus 130 maps the virtual coordinate systems used by the first and second medical apparatuses 120 and 110 to one another based on the selected sectional image and the first medical image (S215). In other words, the medical image registration apparatus 130 matches a first coordinate system that is the virtual coordinate system used by the first medical apparatus 120 and a second coordinate system that is the virtual coordinate system used by the second medical apparatus 110. By performing this coordinate system mapping, it becomes possible to ascertain which portions of the first medical image and the selected sectional image correspond to the same portion of the VOI.

Figure 4:
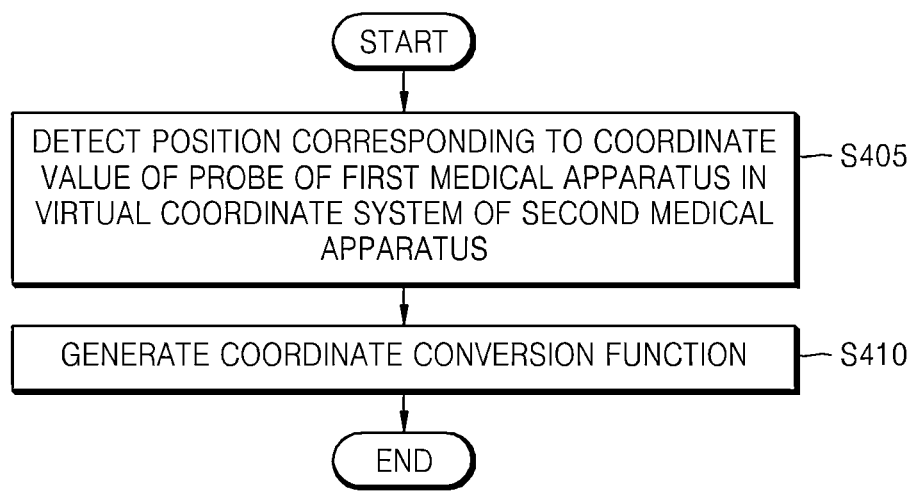
FIG. 4 is a flowchart illustrating a process of generating a coordinate conversion function in the medical image registration method of FIG. 2.

Operation S215 is described in detail with reference to FIG. 4.

The medical image registration apparatus 130 detects a position corresponding to a coordinate value of the probe 121 of the first medical apparatus 120 in the second coordinate system that is a virtual coordinate system of the second medical apparatus 110 (S405). In other words, the medical image registration apparatus 130 detects a position corresponding to a coordinate value of the probe 121 in the first coordinate system that is a virtual coordinate system of the first medical apparatus 120 in the second coordinate system that is a virtual coordinate system of the second medical apparatus 110. This initial step of finding a corresponding position allows alignment of the first and second coordinate system based on a common origin.

Referring to FIG. 10, the position corresponding to the position B1 of the probe 121 in the image 1010 corresponds to a position B2 in the medical images 1030. Such a position is a real-world position in the VOI to which both positions B1 and B2 correspond. The medical image registration apparatus 130 detects the position B2. The medical image registration apparatus 130 then overlays the sectional image 1033 and the first medical image 1020 such that the positions of the segmented anatomic objects in the first medical image 1020 and the sectional image 1033 selected in operation S320 are matched, by aligning the images based on the positions B1 and B2.

If the resolutions of the first and second medical images 1020 and 1030 are different from each other, to match the resolutions, in various embodiments one or both of the images are up-scaled or down-scaled appropriately. When the sectional image 1033 and the first medical image 1020 are overlaid, the medical image registration apparatus 130 sets the position B1 of the probe 121 in the sectional image 1033. Thus, based on analyzing the overlaid images, the medical image registration apparatus 130 may detect in the second coordinate system the position B2 corresponding to the position B1 where the probe is located.

The medical image registration apparatus 130 generates a coordinate conversion function to convert the first coordinate system to the second coordinate system by using a coordinate value of the position B2 that is detected (S410). In other words, the medical image registration apparatus 130 generates a coordinate conversion function to convert a coordinate value of the first coordinate system to a coordinate value of the second coordinate system. Such a function allows the medical image registration apparatus 130 to establish a relationship between areas in the first and second medical images 1020 and 1030.

The coordinate of the position B2 in the second coordinate system is referred to as $T_{init}$. Then, when the probe 121 is moved by a predetermined distance, assuming that the movement of the probe 121 is $T(x,y,z)$ and the rotation of the probe 121 is $R(\psi,\theta,\varphi)$, $T(x,y,z)$ and $R(\psi,\theta,\varphi)$ may be expressed by Equations 1 and 2.

Equation 1

$$T(x, y, z) = \begin{bmatrix} 1 & 0 & 0 & x \\ 0 & 1 & 0 & y \\ 0 & 0 & 1 & z \\ 0 & 0 & 0 & 1 \end{bmatrix}$$

Equation 2

$$R_x(\psi)R_y(\theta)R_x(\phi) =$$

$$\begin{bmatrix} \cos\theta\cos\psi & -\cos\phi\sin\psi+\sin\phi\sin\theta\cos\psi & \sin\phi\sin\psi+\cos\phi\sin\theta\cos\psi & 0 \\ \cos\theta\sin\psi & \cos\phi\cos\psi+\sin\phi\sin\theta\sin\psi & -\sin\phi\cos\psi+\cos\phi\sin\theta\sin\psi & 0 \\ -\sin\theta & \sin\phi\cos\theta & \cos\phi\cos\theta & 0 \\ 0 & 0 & 0 & 1 \end{bmatrix}$$

The medical image registration apparatus 130 may generate a coordinate conversion function M as shown in Equation 3 by using "$T_{init}$", T(x,y,z) and R($\psi,\theta,\varphi$).

$$M=R(\Psi,\theta,\varphi)*T(x,y,z)*T\text{init} \qquad \text{Equation 3}$$

Figure 6:
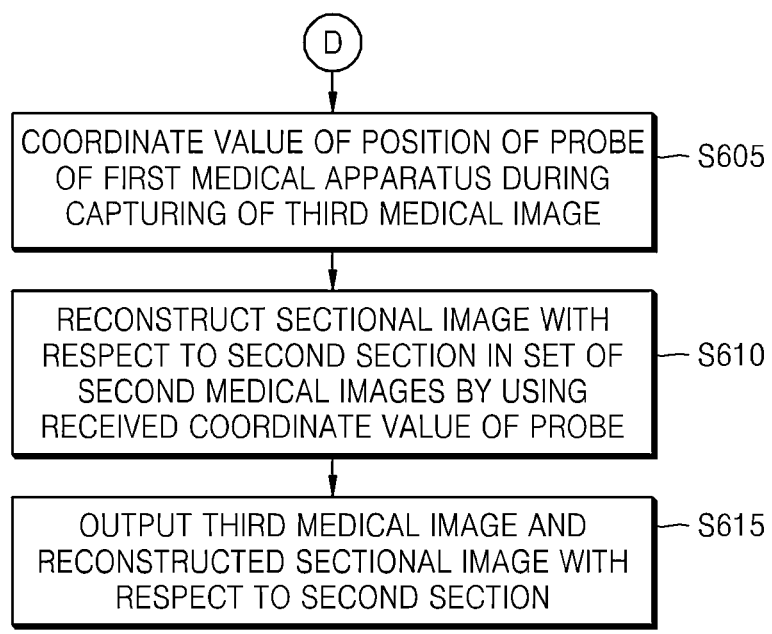
FIG. 6 is a flowchart illustrating a process of outputting an image in the landmark point matching process of FIG. 5.

Referring back to FIG. 2, the medical image registration apparatus 130 tracks a movement of a section captured by the first medical apparatus 120 in the set of second medical images by using a mapped virtual coordinate system (S220). In other words, the medical image registration apparatus 130 tracks a movement of the probe 121 in the set of second medical images, in terms of how the location of the probe 121 changes in the set of second medical images. Such tracking uses the coordinate conversion function of Equation 3. Operation S220 will be described later in detail with reference to descriptions of FIGS. 6 and 8.

Figure 5:
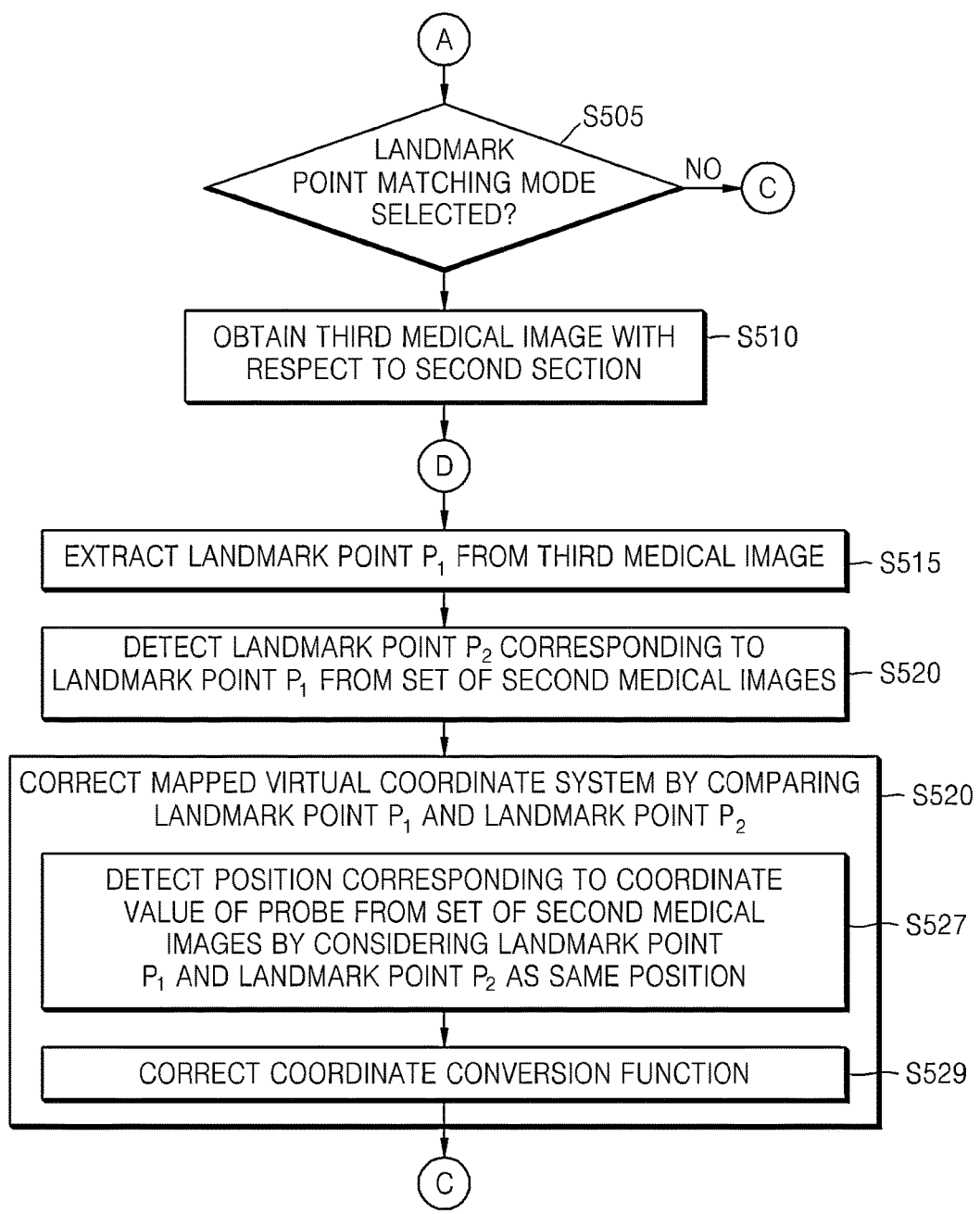
FIG. 5 is a flowchart illustrating a process of matching landmark points and correcting a virtual coordinate system in the medical image registration method of FIG. 2.

FIG. 5 is a flowchart illustrating a process of matching landmark points and correcting a virtual coordinate system in the medical image registration method of FIG. 2. The processes shown in FIG. 5 are optional processes that are omitted in some embodiments. In other words, when the registration result of FIG. 2 provides satisfactory results, the processes of FIG. 5 may be omitted. However, when the registration result of FIG. 2 is not accurate or a more accurate registration result is needed, in an embodiment the processes of FIG. 5 are performed to improve the registration results. The mapping of the first and second coordinate systems by detecting a section corresponding to the first section in FIG. 2 is referred to as plane matching, whereas the matching process of FIG. 5 is referred to as landmark point matching. The landmark point matching of FIG. 5 is described based on an assumption that plane matching has already been performed. Also, descriptions that are the same as those above will be omitted, so the above descriptions are included in the embodiment of FIG. 5 as well.

Referring to FIG. 5, the medical image registration apparatus 130 determines whether a landmark point matching mode is selected (S505). The medical image registration apparatus 130 may display a graphical user interface (GUI) which enables a selection of the landmark point matching mode through a user interface (not shown).

Figure 11:
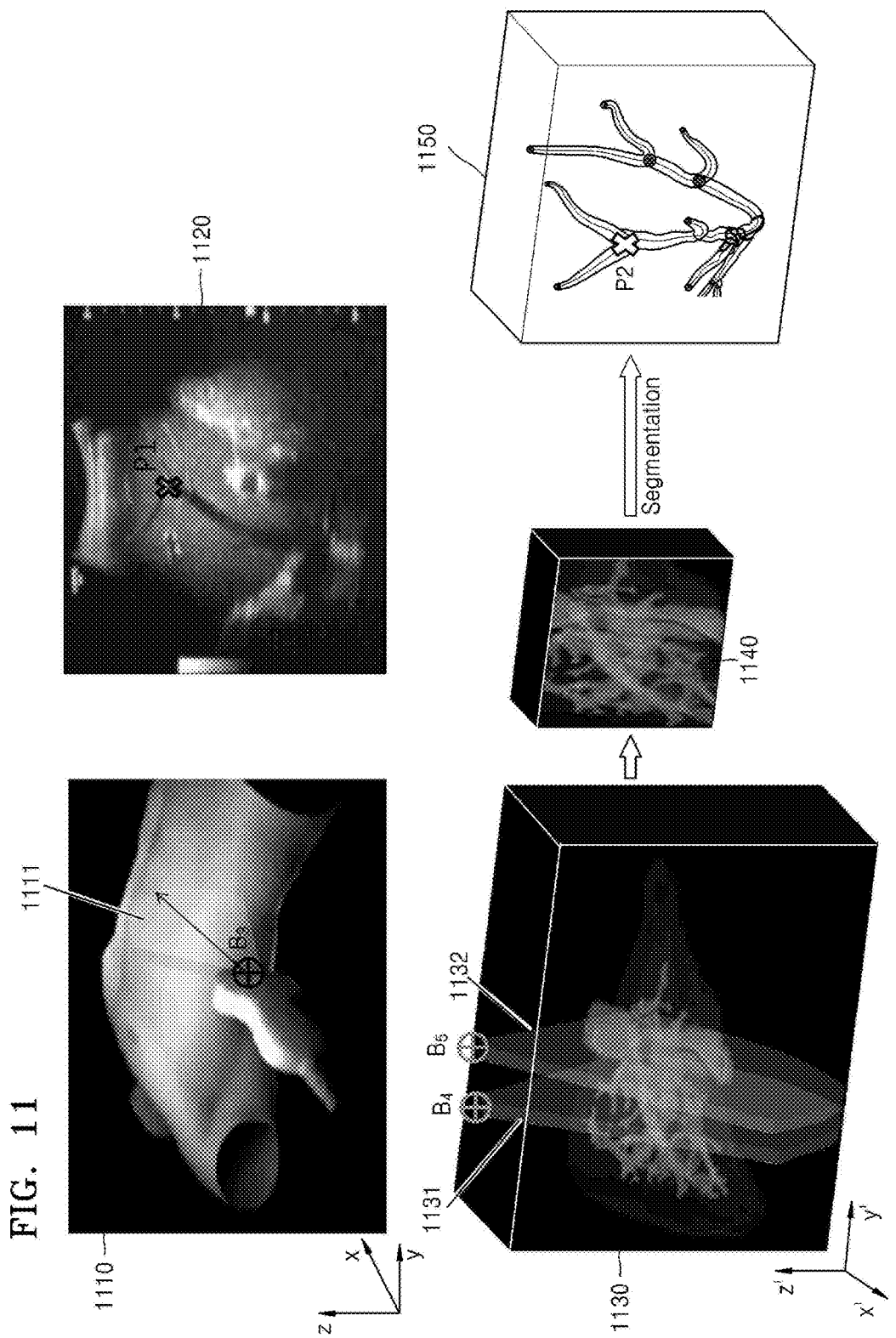
FIG. 11 is an example set of medical images in a landmark point matching process in the medical image registration method of FIG. 2.

When the landmark point matching mode is selected, the medical image registration apparatus 130 obtains a third medical image with respect to a second section captured by the first medical apparatus 120 (S510). In one embodiment, the second section is the same section as the first section. However, to improve accuracy in registration in another embodiment, the second section is different from the first section. Optionally, the second section is selected by a user as in the case of the first section. In an embodiment, the second section is a section crossing the first section. Referring to FIG. 11, the probe 121 rotated by 90° around an x-axis direction captures a second section 1111. A third medical image 1120 is a third medical image captured with respect to the second section 1111.

The third medical image 1120 is displayed, and the medical image registration apparatus 130 may reconstruct a sectional image of the second section 1111 from the set of second medical images and output a reconstructed sectional image (Node D). The node D, which may be omitted according to embodiments, is described in detail with reference to FIG. 6.

The medical image registration apparatus 130 receives a coordinate value of a position B3 of the probe 121 of the first medical apparatus 120 when capturing the third medical image 1120 (S605). The coordinate value of the position B3 may be received separately from the third medical image 1120 or together with the third medical image 1120.

The medical image registration apparatus 130 reconstructs a sectional image with respect to the second section 1111 from the set of second medical images by using a coordinate value of the position B3 (S610). It is assumed in the present embodiment that the second medical images are already reconstructed into a 3D model 1130 according to the above-described MPR method. The medical image registration apparatus 130 detects a position B4 and a section 1131 in the 3D model 1130 by using the coordinate conversion function of Equation 3. Next, the medical image registration apparatus 130 reconstructs an image of the section 1131 from the 3D model 1130. A reconstructed image corresponds to a sectional image with respect to the second section 1111.

The medical image registration apparatus 130 outputs the reconstructed sectional image and the third medical image 1120 in combination with respect to the second image (S615). The reconstructed sectional image and the third medical image 1120 may be output by being overlaid or by being arranged in parallel to each other.

Referring back to FIG. 5, the medical image registration apparatus 130 extracts a landmark point P1 from the third medical image 1120 (S515). In embodiments, the medical image registration apparatus 130 automatically extracts the landmark point P1 according to a landmark point extraction algorithm. On other embodiments, the landmark point P1 is selected based on a user input. When the landmark point P1 is extracted based on a user input, a user may directly set the position of the landmark point P1 in the third medical image 1120, such as through a GUI.

The landmark point is a position that is a reference in image registration and is determined as discussed in the following examples or appropriate alternatives.

Example A. A position that clearly reflects an anatomic feature is determined to be a landmark point. For example, when an object from which a landmark point is to be extracted is a liver, a position where blood vessels are branched in a blood vessel structure in a liver is extracted as a landmark point. When an object from which a landmark point is to be extracted is a heart, a boundary where the left heart and the right heart are divided or a boundary where the main vein and the external heart wall meet is extracted as a landmark point.

Example B. The highest or lowest position of an object from which a landmark point is to be extracted in a given coordinate system is set as a landmark point.

Example C. A position between the landmark points selected by the methods of Example A and Example B may be set to be a landmark point by interpolating the selected landmark points by the methods of Example A and Example B along the surface or edge of an object.

The set landmark point may be presented by a coordinate of x and y axes for a 2D space and by a coordinate of x, y, and z axes for a 3D space. Accordingly, when a coordinate of each landmark point for the 3D space is presented by vectors as $x_0, x_1, \ldots, x_{n-1}$, where "n" denotes the number of landmark points, each landmark point may be expressed by Equation 4.

$$x_{i0} = [x_{i0}, y_{i0}, z_{i0}]$$
$$x_{i1} = [x_{i1}, y_{i1}, z_{i1}]$$
$$\vdots$$
$$x_{in-1} = [x_{in-1}, y_{in-1}, z_{in-1}]$$

Equation 4

In Equation 4, the subscript "i' denotes landmark point coordinate information in the second medical image.

Referring to FIG. 11, the landmark point P1 in the third medical image 1120 is a landmark point extracted by the medical image registration apparatus 130. The medical image registration apparatus 130 detects the landmark point P2 corresponding to the landmark point P1 in the set of second medical images (S520). The process of detecting the landmark point P2 in operation S520 is described in detail with reference to FIG. 7.

Figure 7:
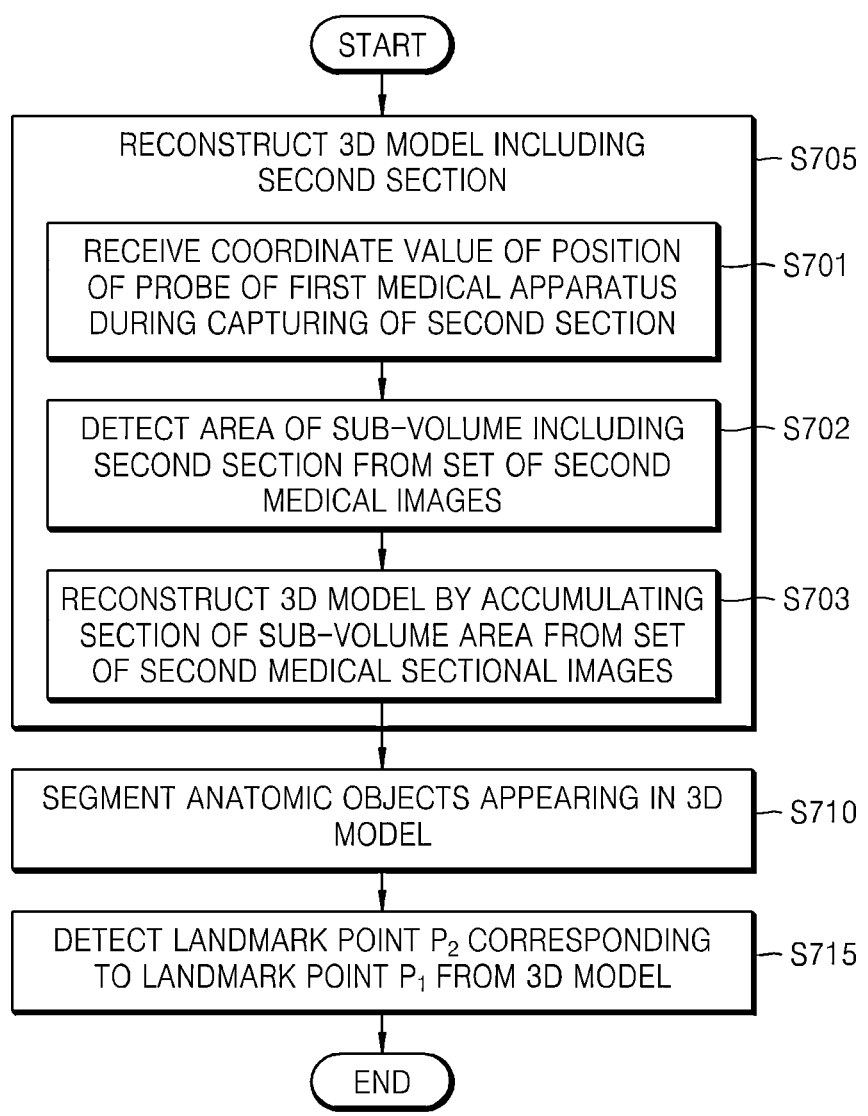
FIG. 7 is a flowchart illustrating a process of detecting a landmark point in the landmark point matching process of FIG. 5.

Referring to FIG. 7, the medical image registration apparatus 130 reconstructs a 3D model including the second section with respect to the VOI (S705). The 3D model may be a 3D model 1130 with respect to the entire VOI or a 3D model 1140 with respect to a sub-volume including a part of the VOI.

In the method of reconstructing the 3D model 1140 with respect to a sub-volume, the medical image registration apparatus 130 receives a coordinate value of the position B3 where the probe 121 of the first medical apparatus 120 is located when capturing the second section (S701).

The medical image registration apparatus 130 detects an area of a sub-volume including the second section from the set of second medical images (S702). The medical image registration apparatus 130 converts a coordinate value of the position B3 to a coordinate value of the position B4 by using the coordinate conversion function of Equation 3. Thus, the medical image registration apparatus 130 may specify the section 1131 in the set of second medical images. The region of a sub-volume is specified by extending the thickness of the section 1131 by a predetermined amount. When extending the thickness, the medical image registration apparatus 130 does not extend the region of a sub-volume with respect to a region where the anatomic object does not exist.

The medical image registration apparatus 130 reconstructs the 3D model 1140 by accumulating sections of the sub-volume area from set of second medical images (S703). The above-described MPR method may be used to reconstruct the 3D model 1140. As illustrated in FIG. 11, the 3D model 1140 with respect to the sub-volume has a smaller volume than that of the whole 3D model 1130 with respect to the VOI. Thus, the time for searching for the landmark point P2 in the 3D model 1140 with respect to the sub-volume may be less than the time for searching for the landmark point P2 in the whole 3D model 1130 with respect to the volume because a smaller quantity of data defines the sub-volume and hence it will take less time to process.

The medical image registration apparatus 130 segments the anatomic objects in the 3D model 1140 (S710). In other words, the medical image registration apparatus 130 segments the anatomic objects in the 3D model 1140, rather than in a two dimensional model. Segmenting the 3D model may be especially helpful because it indicates the overall distribution of an anatomic object in a VOI. A blood vessel structure 1150 of FIG. 11 is the anatomic object segmented from the 3D model 1140. Also, the medical image registration apparatus 130 segments the anatomic objects appearing in the third medical image. As described above, in examples a graph cut technique or a GMM technique are used for the segmentation.

The medical image registration apparatus 130 detects the landmark point P2 corresponding to the landmark point P1 from the 3D model 1140 (S715). The medical image registration apparatus 130 compares the anatomic objects segmented from the 3D model 1140 and the anatomic objects segmented from the third medical image. The anatomic objects segmented from the 3D model 1140 are 3D objects, whereas the anatomic objects segmented from the third medical image are 2D objects. Thus, the medical image registration apparatus 130 compares a volume and a plane. In other words, the medical image registration apparatus 130 searches for the most similar section to the plane in the volume while rotating and moving the plane within the volume. To find the most similar section to the plane, the above-described Gabor wavelet technique or the local binary pattern matching technique may be used. If the third medical image corresponds to the 3D model 1140, there should be an alignment, including a location and orientation, which represents the best correspondence between the third medical image and the 3D model 1140, as if the third medical image had been obtained as a section of the 3D model 1140, derived from that location and orientation.

The medical image registration apparatus 130 detects the landmark point P2 corresponding to the landmark point P1 from the 3D model 1140 by matching the positions of the anatomic objects on the plane in the 3D model 1140 and the anatomic objects appearing in the third medical image.

Referring back to FIG. 5, the medical image registration apparatus 130 compares the landmark point P1 and the landmark point P2 and corrects a mapped virtual coordinate system (S520). When the landmark point P1 is considered to be the landmark point P2, the medical image registration apparatus 130 detects from the set of second medical images a position B5 corresponding to the position B3 of the probe 121 during capturing of the third medical image (S527). Referring to FIG. 11, the position B5 in the 3D model 1130 indicates a position corresponding to the position B3 of the probe 121 when the landmark point P1 and the landmark point P2 are matched. In other words, although the position corresponding to the position B3 of the probe 121 was the position B4 before the landmark point matching is performed, the position is corrected to the position B5. Thus, in an embodiment, as the position of the position B4 is moved to the position B5, an error in the plane matching result is corrected.

The medical image registration apparatus 130 corrects the coordinate conversion function (S529). The medical image registration apparatus 130 corrects the coordinate conversion function to convert a coordinate value of the position B3 in the first coordinate system to a coordinate value of the position B5 in the second coordinate system. In one embodiment, the medical image registration apparatus 130 corrects values of the coordinate conversion function which has been generated by the plane matching. According to another embodiment, the medical image registration apparatus 130 generates a new coordinate conversion function instead of the correction of the values of the coordinate conversion function using Equations 1 through 3. Whether the coordinate conversion function is corrected or generated anew, afterwards the coordinate conversion function produces coordinate conversions that fixes the identified discrepancy.

Figure 8:
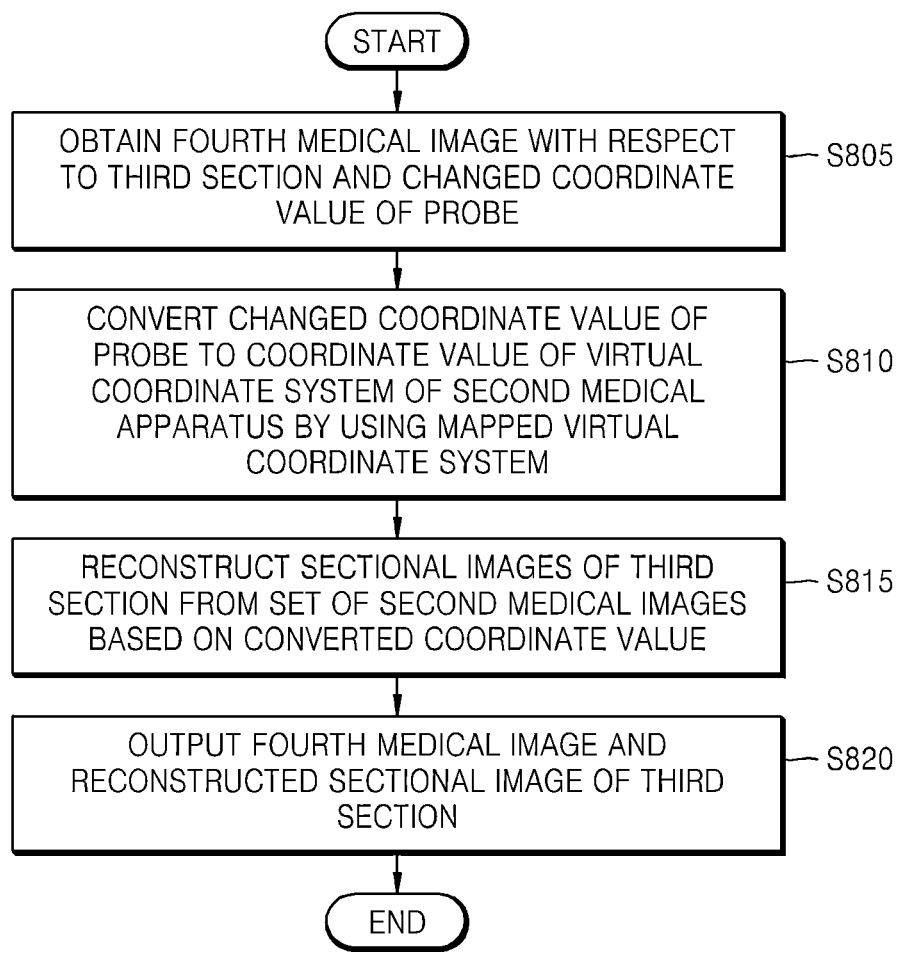
FIG. 8 is a flowchart illustrating a process of outputting a matched image according to an embodiment of the present invention.

FIG. 8 is a flowchart illustrating a process of outputting a matched image according to an embodiment of the present invention. In an embodiment, the processes of FIG. 8 are performed at a node C of FIG. 5.

The medical image registration apparatus 130 obtains a fourth medical image captured by the first medical apparatus 120 with respect to a third section and a coordinate value of the probe 121 moved to capture the fourth medical image (S805). A coordinate value of the probe 121 is a coordinate value of a position B6 of the probe 121 in the first coordinate system and may be obtained together with the fourth medical image (S805).

The medical image registration apparatus 130 converts the coordinate value of the probe 121 to a coordinate value of the second coordinate system by using the mapped virtual coordinate system (S810). In other words, the medical image registration apparatus 130 converts the coordinate value of the position B6 in the first coordinate system to a coordinate value of a position B7 of the second coordinate system.

The medical image registration apparatus 130 reconstructs a sectional image of the third section from the set of second medical images based on a converted coordinate value (S815). It is assumed that the second medical images are already reconstructed into a 3D model according to the above-described MPR method. The medical image registration apparatus 130 detects the position B6 and the third section in the 3D model by using the coordinate conversion function. The medical image registration apparatus 130 reconstructs the sectional image of the third section from the 3D model.

The medical image registration apparatus 130 outputs the sectional image reconstructed with respect to the third section and the fourth medical image in combination (S820). For example, the reconstructed sectional image and the fourth medical image 1120 are output by being overlaid or arranged parallel to each other.

Figure 9A:
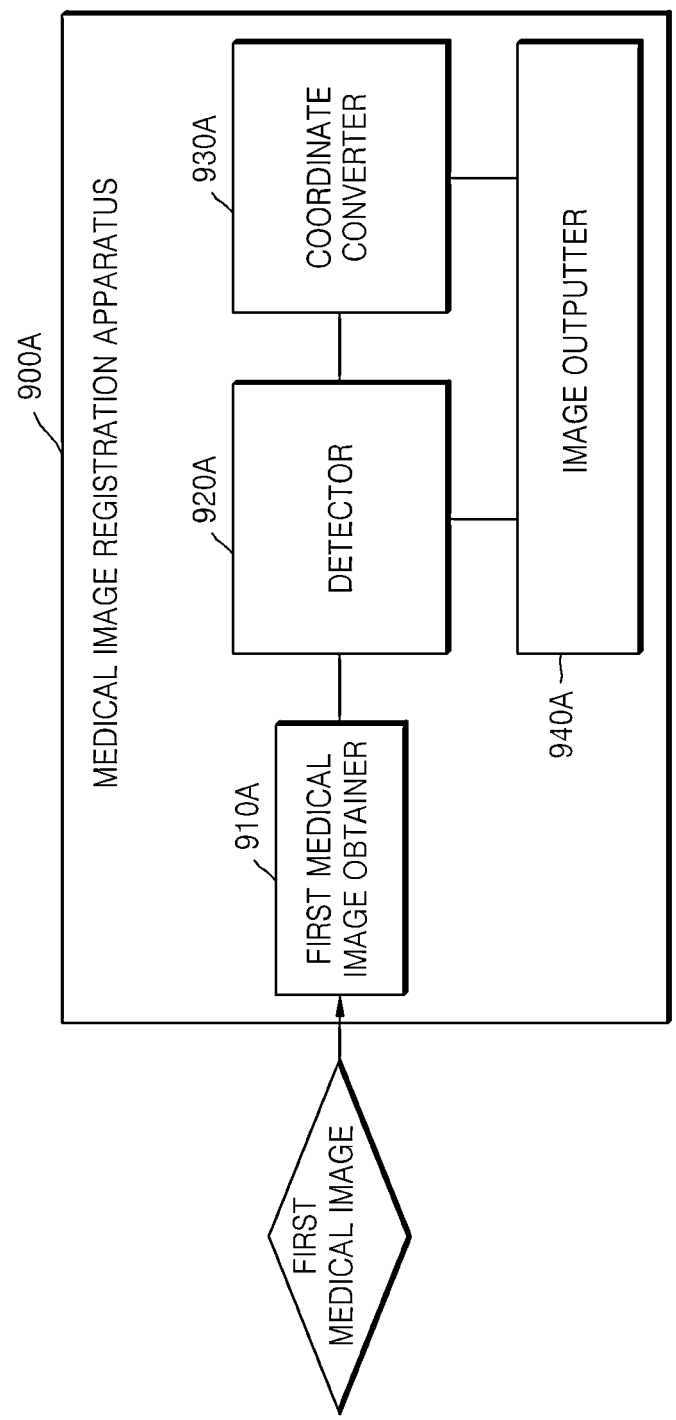
FIG. 9A is a block diagram of a medical image registration apparatus according to an embodiment of the present invention.

FIG. 9A is a block diagram of a medical image registration apparatus 900A according to an embodiment of the present invention. The above descriptions related to FIGS. 1 through 8 may be referred for the medical image registration apparatus 900A of FIG. 9A.

Referring to FIG. 9A, the medical image registration apparatus 900A includes a first medical image obtainer 910A, a detector 920A, a coordinate converter 930A, and an image outputter 940A.

The first medical image obtainer 910A obtains a first medical image captured by the first medical apparatus 120 with respect to a first section selected from a VOI. The first section is a section selected in the middle of capturing an image by using the first medical apparatus 120. Optionally, a user selects a section in a direction parallel to a section along which the second medical images are captured.

The detector 920A detects a sectional image corresponding to the first section from a set of the second medical images previously captured with respect to the VOI based on an anatomical feature appearing in the first medical image.

The coordinate converter 930A maps virtual coordinate systems used by the first and second medical apparatuses 120 and 110 based on the detected sectional image and the first medical image.

The image outputter 940A tracks a movement of a section captured by the first medical apparatus 120 from the set of second medical images by using the mapped virtual coordinate system.

A detailed structure of the medical image registration apparatus 900A is described below with reference to FIG. 9B. The above descriptions about FIGS. 1 through 9A may be referred to for a medical image registration apparatus 900B of FIG. 9B.

Figure 9B:
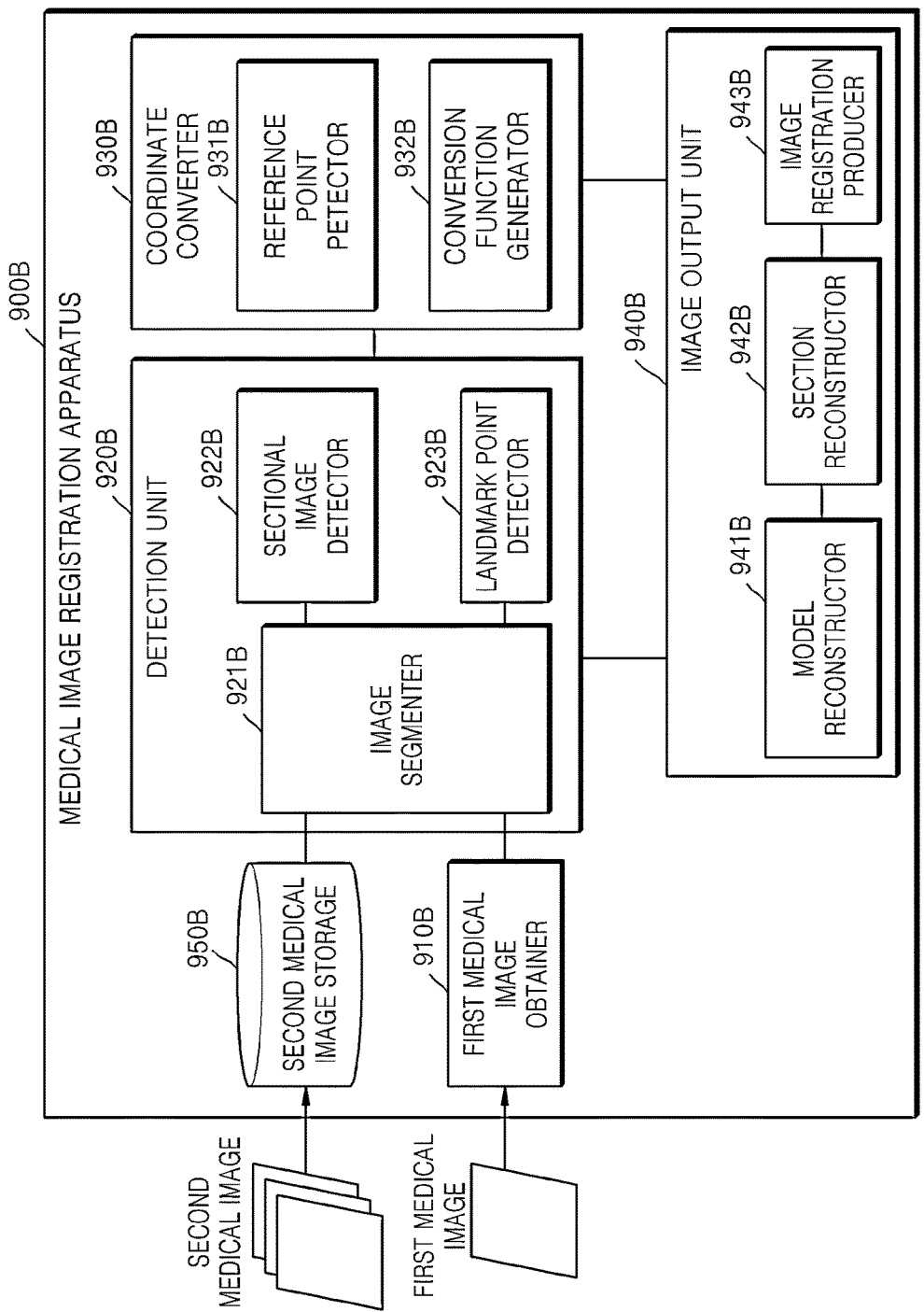
FIG. 9B is a block diagram illustrating a detailed structure of the medical image registration apparatus of FIG. 9A.

Referring to FIG. 9B, the medical image registration apparatus 900B includes a first medical image obtainer 910B, a detector 920B, a coordinate converter 930B, an image outputter 940B, and a second medical image storage 950B. For convenience of explanation, the operations of the medical image registration apparatus 900B for plane matching and landmark point matching will be separately described as follows.

The second medical image storage 950B stores a set of second medical images captured by the second medical apparatus 110 before a medical treatment. Coordinate values of the second coordinate system with respect to the positions where the second medical images were captured are mapped in each of the second medical images.

The detector 920B includes an image segmenter 921B, a sectional image detector 922B, and a landmark point detector 923B. The sectional image detector 922B detects a sectional image corresponding to the first section from the set of second medical images based on an anatomical feature appearing in the first medical image. The sectional image detector 922B detects a sectional image based on a similarity in anatomic objects appearing in the first medical image and the set of second medical images.

In the plane matching, the image segmenter 921B segments the anatomic objects appearing in the first medical image and the anatomic objects appearing in the set of second medical images. For example, the image segmenter 921B segments at least one of organs, blood vessels, and lesions appearing in the first medical image and the set of second medical images based on at least one of the graph cut technique and the GMM technique.

In plane matching, the sectional image detector 922B calculates a similarity between the segmented anatomic objects in the first medical image and the segmented anatomic objects in the set of second medical images, and selects a section image having the highest calculated similarity among the set of second medical images. In examples, as discussed above, the sectional image detector 922B calculates a similarity between the segmented anatomic objects based on at least one of the Gabor wavelet technique and the local binary pattern matching technique. In landmark point matching, the landmark point detector 923B extracts the landmark point P1 from the third medical image and detects the landmark point P2 corresponding to the extracted landmark point P1 from the set of second medical images. The operation of the medical image registration apparatus 900B in the landmark point matching will be described later below.

The coordinate converter 930B includes a reference point detector 931B and a conversion function generator 932B. The reference point detector 931B detects the position B2 corresponding to the position B1 of the probe 121 of the first medical apparatus 120 in the virtual coordinate system of the first medical apparatus 120 from the virtual coordinate system of the second medical apparatus 110.

The conversion function generator 932B generates a coordinate conversion function to convert the virtual coordinate system of the first medical apparatus 120 to the virtual coordinate system of the second medical apparatus 110 by using a coordinate value of the position B2. The image outputter 940B tracks a movement of the section by using a generated coordinate conversion function.

The operation of the medical image registration apparatus 900B during landmark point matching is described below. It is assumed that a model reconstructor 941B reconstructs a 3D model of a VOI by using the set of second medical images.

The first medical image obtainer 910B obtains the third medical image captured by the first medical apparatus 120 with respect to the second section selected from the VOI. In an embodiment, a coordinate value of the position B3 of the probe 121 is obtained with the third medical image. The reference point detector 931B converts the coordinate value of the position B3 to a coordinate value of the position B4 in the 3D model 1130 by using the coordinate conversion function of Equation 3. A section reconstructor 942B reconstructs an image of the section 1131 from the 3D model 1130. A reconstructed image corresponds to a sectional image with respect to the second section 1111. An image registration producer 943B outputs the third medical image 1120 and the reconstructed sectional image with respect to the second section in combination. For example, the reconstructed sectional image and the third medical image 1120 are output by being overlaid or arranged parallel to each other.

The landmark point detector 923B extracts the landmark point P1 from the third medical image and detects the landmark point P2 corresponding to the extracted landmark point P1. The landmark point detector 923B may automatically extract the landmark point P1 according to a landmark point extraction algorithm or based on a user input. The model reconstructor 941B reconstructs the 3D model 1140 with respect to a sub-volume. The method of reconstructing the 3D model 1140 with respect to the sub-volume is described above with reference to FIG. 7. The image segmenter 921B segments the anatomic objects appearing in the third medical image.

Next, the landmark point detector 923B compares the anatomic objects segmented in the 3D model 1140 and the anatomic objects segmented in the third medical image and detects the landmark point P2 corresponding to the landmark point P1 from the 3D model 1140.

The coordinate convertor 930B corrects the mapped virtual coordinate system based on the extracted landmark point P1 and the detected landmark point P2. When the landmark point P1 and the landmark point P2 are considered to be the same position, the reference point detector 931B detects the position B5 corresponding to the position B3 of the probe 121 when capturing the third medical image. The coordinate conversion function generator 932B corrects the coordinate conversion function such that the coordinate value of the position B3 in the first coordinate system may be converted to the coordinate value of the position B5 in the second coordinate system.

The operations of the medical image registration apparatus 900B when performing the plane matching and the landmark point matching are described above. The operation of the medical image registration apparatus 900B when tracking a movement of a section captured by the first medical apparatus 120 in the set of second medical images by using the mapped virtual coordinate system will now be described below.

The first medical image obtainer 910B obtains the fourth medical image captured by the first medical apparatus 120 with respect to the third section and a coordinate value of the probe 121 that is moved to capture the fourth medical image.

The coordinate converter 930B converts the coordinate value of the probe 121 to the coordinate value of the second coordinate system by using the mapped virtual coordinate system.

The section reconstructor 942B reconstructs a sectional image of the third section from the set of second medical images based on the converted coordinate value. For example, a 3D model of a VOI reconstructed by the model reconstructor 941B is continuously used. The reference point detector 931B detects the position B6 in the 3D model and the third section by using the coordinate conversion function. The section reconstructor 942B reconstructs a sectional image of the third section from the 3D model by using the detected position B6 and the third section.

The image registration producer 943B outputs a reconstructed sectional image with respect to the third section and the fourth medical image. For example, reconstructed sectional image and the fourth medical image 1120 are output by being overlaid or arranged parallel to each other.

The image output by the image outputter 940B is displayed on the image display apparatus 140.

A hardware component may be, for example, a physical device that physically performs one or more operations, but is not limited thereto. Examples of hardware components include microphones, amplifiers, low-pass filters, high-pass filters, band-pass filters, analog-to-digital converters, digital-to-analog converters, and processing devices.

A processing device may be implemented using one or more general-purpose or special-purpose computers, such as, for example, a processor, a controller and an arithmetic logic unit, a digital signal processor, a microcomputer, a field-programmable array, a programmable logic unit, a microprocessor, or any other device capable of running software or executing instructions. The processing device may run an operating system (OS), and may run one or more software applications that operate under the OS. The processing device may access, store, manipulate, process, and create data when running the software or executing the instructions. For simplicity, the singular term "processing device" may be used in the description, but one of ordinary skill in the art will appreciate that a processing device may include multiple processing elements and multiple types of processing elements. For example, a processing device may include one or more processors, or one or more processors and one or more controllers. In addition, different processing configurations are possible, such as parallel processors or multi-core processors.

Software or instructions for controlling a processing device to implement a software component may include a computer program, a piece of code, an instruction, or some combination thereof, for independently or collectively instructing or configuring the processing device to perform one or more desired operations. The software or instructions may include machine code that may be directly executed by the processing device, such as machine code produced by a compiler, and/or higher-level code that may be executed by the processing device using an interpreter. The software or instructions and any associated data, data files, and data structures may be embodied permanently or temporarily in any type of machine, component, physical or virtual equipment, computer storage medium or device, or a propagated signal wave capable of providing instructions or data to or being interpreted by the processing device. The software or instructions and any associated data, data files, and data structures also may be distributed over network-coupled computer systems so that the software or instructions and any associated data, data files, and data structures are stored and executed in a distributed fashion.

For example, the software or instructions and any associated data, data files, and data structures may be recorded, stored, or fixed in one or more non-transitory computer-readable storage media. A non-transitory computer-readable storage medium may be any data storage device that is capable of storing the software or instructions and any associated data, data files, and data structures so that they can be read by a computer system or processing device. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMS, BD-ROMs, BD-Rs, BD-R LTHs, BD-REs, magnetic tapes, floppy disks, magneto-optical data storage devices, optical data storage devices, hard disks, solid-state disks, or any other non-transitory computer-readable storage medium known to one of ordinary skill in the art.

As a non-exhaustive illustration only, a terminal/device/unit described herein may be a mobile device, such as a cellular phone, a personal digital assistant (PDA), a digital camera, a portable game console, an MP3 player, a portable/personal multimedia player (PMP), a handheld e-book, a portable laptop PC, a global positioning system (GPS) navigation device, a tablet, a sensor, or a stationary device, such as a desktop PC, a high-definition television (HDTV), a DVD player, a Blue-ray player, a set-top box, a home appliance, or any other device known to one of ordinary skill in the art that is capable of wireless communication and/or network communication.

A computing system or a computer may include a microprocessor that is electrically connected to a bus, a user interface, and a memory controller, and may further include a flash memory device. The flash memory device may store N-bit data via the memory controller. The N-bit data may be data that has been processed and/or is to be processed by the microprocessor, and N may be an integer equal to or greater than 1. If the computing system or computer is a mobile device, a battery may be provided to supply power to operate the computing system or computer. It will be apparent to one of ordinary skill in the art that the computing system or computer may further include an application chipset, a camera image processor, a mobile Dynamic Random Access Memory (DRAM), and any other device known to one of ordinary skill in the art to be included in a computing system or computer. The memory controller and the flash memory device may constitute a solid-state drive or disk (SSD) that uses a non-volatile memory to store data.

The invention may also be embodied as computer readable codes on a computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, optical data storage devices, etc.

As described above, according to the one or more of the above embodiments of the present invention, when medical images captured by first and second medical apparatuses are matched with each other, registration may be performed more accurately and quickly by omitting the complicated and inconvenient manual registration process.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure. It should be understood that the exemplary embodiments described herein should be considered in a descriptive sense only and not for purposes of limitation. Descriptions of features or aspects within each embodiment should typically be considered as available for other features or aspects in other embodiments.

What is claimed is:

1. A method of medical image registration with respect to a volume of interest (VOI), comprising:

obtaining, by a processor, a first medical image corresponding to a selected section of the VOI, from a first medical apparatus;

detecting automatically, by the processor, a sectional image corresponding to the selected section of the VOI from second medical images previously obtained of the VOI from a second medical apparatus, based on an anatomical feature appearing in the first medical image;

detecting, by a sensor of the first medical apparatus, a first position in a first virtual coordinate scheme of the first medical apparatus, wherein the first position indicates a location of a probe included in the first medical apparatus;

overlaying the first medical image and the sectional image by matching the anatomical feature appearing in the first medical image to an anatomical feature appearing in the sectional image;

detecting automatically based on the overlay, by the processor, a second position in a second virtual coordinate scheme of the second medical apparatus, wherein the second position corresponds to the first position and indicates the location of the probe in the second virtual coordinate scheme;

generating, by the processor, a coordinate conversion function to convert the first virtual coordinate scheme of the first medical apparatus to the second virtual coordinate scheme of the second medical apparatus by using a coordinate value of the second position;

mapping, by the processor, the first virtual coordinate scheme of the first medical apparatus and the second virtual coordinate scheme of the second medical apparatus to produce a mapped virtual coordinate scheme, based on the coordinate conversion function;

tracking, by the processor, a movement of a section of the VOI obtained by the first medical apparatus in the second medical images by using the mapped virtual coordinate scheme;

reconstructing, by the processor, a sectional image corresponding to the moved section of the VOI from the second medical images based on the mapped virtual coordinate scheme; and outputting, by the processor, an image corresponding to the moved section of the VOI obtained by the first medical apparatus and the reconstructed sectional image with respect to the moved section of the VOI.

2. The method of claim 1, wherein the detecting of the sectional image comprises:

detecting, by the processor, the sectional image based on a similarity between the anatomical feature appearing in the first medical image and anatomical features appearing in the second medical images.

3. The method of claim 1, wherein the detecting of the sectional image comprises:
segmenting, by the processor, anatomic objects appearing in the first medical image and anatomic objects appearing in the second medical images;
calculating, by the processor, a similarity between the segmented anatomic objects in the first medical image and the segmented anatomic objects in the second medical images; and
selecting, by the processor, a sectional image having the highest calculated similarity among the second medical images.

4. The method of claim 3, wherein the segmenting of the anatomic objects comprises:
segmenting, by the processor, at least one of organs, blood vessels, and lesions appearing in the first medical image and the second medical images based on at least one of a graph cut technique and a Gaussian mixture model (GMM) technique, and
wherein the calculating of the similarity comprises:
calculating, by the processor, the similarity between the segmented anatomic objects based on at least one of a Gabor wavelet technique and a local binary pattern matching technique.

5. The method of claim 1, further comprising:
obtaining, by the processor, a third medical image obtained by the first medical apparatus with respect to a second section selected in the VOI;
extracting, by the processor, a first landmark point from the third medical image;
detecting, by the processor, a second landmark point corresponding to the extracted first landmark point from the second medical images; and
correcting, by the processor, the mapped virtual coordinate scheme based on the extracted first landmark point and the detected second landmark point.

6. The method of claim 5, wherein the detecting of the second landmark point comprises:
reconstructing, by the processor, a three-dimensional (3D) model with respect to the VOI by using the second medical images;
segmenting, by the processor, each of anatomic objects appearing in the reconstructed 3D model and the third medical image; and
detecting, by the processor, the second landmark point corresponding to the first landmark point from the reconstructed 3D model by comparing the segmented anatomic objects in the reconstructed 3D model and the third medical image.

7. The method of claim 5, wherein, in the correcting of the mapped virtual coordinate scheme, the coordinate conversion function is corrected such that the first landmark point and the second landmark point are matched with each other, and in the tracking of the movement of the section, the movement of the section is tracked by using the corrected coordinate conversion function.

8. The method of claim 1, wherein the tracking of the movement of the section comprises:
obtaining, by the processor, a fourth medical image obtained by the first medical apparatus with respect to a third section selected in the VOI as the probe of the first medical apparatus moves;
converting, by the processor, a coordinate value of a position of the probe of the first medical apparatus during capturing of the fourth medical image to a coordinate value of the second virtual coordinate scheme of the second medical apparatus based on the mapped virtual coordinate scheme; and
reconstructing, by the processor, a sectional image with respect to the third section from the second medical images based on the converted coordinate value of the second virtual coordinate scheme.

9. The method of claim 8, further comprising outputting the fourth medical image and the reconstructed sectional image with respect to the third section.

10. The method of claim 1, wherein the first medical apparatus is an ultrasonography machine and the second medical apparatus is a computed tomography (CT) imaging device, magnetic resonance (MR) imaging device or positron emission tomography (PET) device.

11. The method of claim 1, wherein the coordinate conversion function comprises a translation and a rotation.

12. The method of claim 1, wherein the coordinate conversion function is expressed as equation:

$$M = R(\Psi,\theta,\varphi) * T(x,y,z) * T\text{init}$$

wherein $R(\Psi,\theta,\varphi)$ represents rotation of the probe and is expressed as equation:

$$R_z(\psi)R_y(\theta)R_x(\phi) = \begin{bmatrix} \cos\theta\cos\psi & -\cos\phi\sin\psi + \sin\phi\sin\theta\cos\psi & \sin\phi\sin\psi + \cos\phi\sin\theta\cos\psi & 0 \\ \cos\theta\sin\psi & \cos\phi\cos\psi + \sin\phi\sin\theta\sin\psi & -\sin\phi\cos\psi + \cos\phi\sin\theta\sin\psi & 0 \\ -\sin\theta & \sin\phi\cos\theta & \cos\phi\cos\theta & 0 \\ 0 & 0 & 0 & 1 \end{bmatrix},$$

wherein $T(x,y,z)$ represents translation of the probe and is expressed as equation:

$$T(x, y, z) = \begin{bmatrix} 1 & 0 & 0 & x \\ 0 & 1 & 0 & y \\ 0 & 0 & 1 & z \\ 0 & 0 & 0 & 1 \end{bmatrix},$$

and wherein $T_{init}$ denotes the second position in the second virtual coordinate scheme.

13. An apparatus for medical image registration, comprising:
a processor configured to:
obtain a first medical image corresponding to a selected section of a volume of interest (VOI), from a first medical apparatus,
detect automatically a sectional image corresponding to the selected section of the VOI from second medical images previously obtained of the VOI from a second medical apparatus, based on an anatomical feature appearing in the first medical image,
receive, from a sensor of the first medical apparatus, data related to a first position in a first virtual coordinate scheme of the first medical apparatus, wherein the first position indicates a location of a probe included in the first medical apparatus, overlay the first medical image and the sectional image by matching the anatomical feature appearing in the first medical image to an anatomical feature appearing in the sectional image, detect automatically, based on the overlay, a second position in a second virtual coordinate scheme of the second medical apparatus, wherein the second position corresponds to the first position and indicates the location of the probe in the second virtual coordinate scheme, generate a coordinate conversion function to convert the first virtual coordinate scheme of the first medical apparatus to the second virtual coordinate scheme of the second medical apparatus by using a coordinate value of the second position, map the first virtual coordinate scheme of the first medical apparatus and the second virtual coordinate scheme of the second medical apparatus to produce a mapped virtual coordinate scheme, based on the coordinate conversion function, track a movement of a section of the VOI obtained by the first medical apparatus in the second medical images by using the mapped virtual coordinate scheme, reconstruct a sectional image corresponding to the moved section of the VOI from the second medical images based on the mapped virtual coordinate scheme, and output an image corresponding to the moved section of the VOI obtained by the first medical apparatus and the reconstructed sectional image with respect to the moved section of the VOI.

14. The apparatus of claim 13, wherein the processor is further configured to detect the sectional image based on a similarity between the anatomical feature appearing in the first medical image and anatomical features appearing in the second medical images.

15. The apparatus of claim 13, wherein the processor is further configured to:
segment anatomic objects appearing in the first medical image and anatomic objects appearing in the second medical images,
calculate a similarity between the segmented anatomic objects in the first medical image and the segmented anatomic objects in the second medical images, and
select a sectional image having the highest calculated similarity among the second medical images.

16. The apparatus of claim 15, wherein the processor is further configured to:
segment at least one of organs, blood vessels, and lesions appearing in the first medical image and the second medical images based on at least one of a graph cut technique and a Gaussian mixture model (GMM) technique, and
calculate the similarity between the segmented anatomic objects based on at least one of a Gabor wavelet technique and a local binary pattern matching technique.

17. The apparatus of claim 13, wherein the processor is further configured to:
obtain a third medical image obtained by the first medical apparatus with respect to a second section selected in the VOI,
extract a first landmark point from the third medical image,
detect a second landmark point corresponding to the extracted first landmark point from the second medical images, and
correct the mapped virtual coordinate scheme based on the extracted first landmark point and the detected second landmark point.

18. The apparatus of claim 17, wherein processor is further configured to:
reconstruct a three-dimensional (3D) model with respect to the VOI by using the second medical images,
segment each of anatomic objects appearing in the reconstructed 3D model and the third medical image, and
detect the second landmark point corresponding to the first landmark point from the reconstructed 3D model by comparing the segmented anatomic objects in the reconstructed 3D model and the third medical image.

19. The apparatus of claim 17, wherein the processor is further configured to correct the coordinate conversion function such that the first landmark point and the second landmark point are matched with each other, and track the movement of the section by using the corrected coordinate conversion function.

20. The apparatus of claim 13, wherein the processor is further configured to:
obtain a fourth medical image obtained by the first medical apparatus with respect to a third section selected in the VOI as the probe of the first medical apparatus moves,
convert a coordinate value of a position of the probe of the first medical apparatus during capturing of the fourth medical image to a coordinate value of the second virtual coordinate scheme of the second medical apparatus based on the mapped virtual coordinate scheme, and
reconstruct a sectional image with respect to the third section from the second medical images based on the converted coordinate value of the second virtual coordinate scheme.

21. The apparatus of claim 20, wherein the processor is further configured to output the fourth medical image and the reconstructed sectional image with respect to the third section.

22. The apparatus of claim 13, wherein the first medical apparatus is an ultrasonography machine and the second medical apparatus is a computed tomography (CT) imaging device, magnetic resonance (MR) imaging device or positron emission tomography (PET) device.

* * * * *